(12) United States Patent
Raines et al.

(10) Patent No.: US 11,673,865 B2
(45) Date of Patent: Jun. 13, 2023

(54) CYCLOOCTYNES FOR CLICK CHEMISTRY

(71) Applicant: Massachusetts Institute of Technology, Cambridge, MA (US)

(72) Inventors: Ronald T. Raines, Cambridge, MA (US); Brian Gold, Albuquerque, NM (US); Jesus M. Dones, Princeton, NJ (US); Nile S. Abularrage, Boston, MA (US); Brian James Graham, Belmont, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 17/661,440

(22) Filed: Apr. 29, 2022

(65) Prior Publication Data

US 2022/0402876 A1 Dec. 22, 2022

Related U.S. Application Data

(62) Division of application No. 17/332,941, filed on May 27, 2021.

(51) Int. Cl.
| | | |
|---|---|---|
| *C07D 221/16* | (2006.01) | |
| *C07D 471/04* | (2006.01) | |
| *C07D 249/16* | (2006.01) | |
| *C07D 231/54* | (2006.01) | |
| *C07C 13/547* | (2006.01) | |

(52) U.S. Cl.
CPC .......... *C07D 221/16* (2013.01); *C07C 13/547* (2013.01); *C07D 231/54* (2013.01); *C07D 249/16* (2013.01); *C07D 471/04* (2013.01); *C07C 2603/36* (2017.05)

(58) Field of Classification Search
CPC ........................... C07C 13/547; C07D 221/16
See application file for complete search history.

(56) References Cited

U.S. PATENT DOCUMENTS 9,932,297 B2 * 4/2018 Boons ................ A61K 49/0021

* cited by examiner

*Primary Examiner* — Kamal A Saeed
(74) *Attorney, Agent, or Firm* — Lathrop GPM LLP; Laura A. Labeots

(57) ABSTRACT

Provided herein are dibenzocyclooctyne compounds useful as reagents in 1,3-dipolar cycloaddition reactions, and methods for their preparation.

8 Claims, 4 Drawing Sheets

CYCLOOCTYNES FOR CLICK CHEMISTRY

CROSS REFERENCE TO RELATED APPLICATIONS

This application is a divisional application of pending U.S. patent application Ser. No. 17/332,941, filed on May 27, 2021, the content of which application is incorporated herein by reference in its entirety.

STATEMENT REGARDING FEDERALLY SPONSORED RESEARCH OR DEVELOPMENT

This invention was made with Government support under Grant No. R01 GM044783 awarded by the National Institutes of Health (NIH). The Government has certain rights in the invention.

BACKGROUND

The discovery of "spring-loaded"[1] but chemoselective reactions has widespread application in chemical biology, polymer chemistry, and materials chemistry. In this realm, a particular 1,3-dipolar cycloaddition[2]—the strain-promoted azide-alkyne cycloaddition (SPAAC)[3-5]—has been at the forefront. Its preeminence is attributable to the attractive features of the azido group[6-8] along with the formation of an aromatic product,[9,10] enabling high chemoselectivity.[11,12]

Efforts to both understand[13-22] and optimize[23-28] SPAAC reactivity have focused on two general strategies: (1) increasing strain (i.e., pre-distortion), and (2) tuning electronics.[29-31] After the discovery of the reactivity of cycloalkynes in SPAAC in chemical contexts,[3-5] the utility of cyclooctyne (OCT) was demonstrated in a biological context.[6] Installing fluoro groups at the propargylic position via a 12-step synthetic route generated DIFO[23] and further increased reaction rates. Theoretical investigations attributed the higher reactivity to LUMO-lowering,[14,18] though specific orbital interactions that elicit a low-energy transition state (TS) have become apparent.[20,21] The exocyclic fluoro groups are gauche relative to the forming C—N bonds. In contrast, optimal orbital overlap (i.e., anti-periplanar) is achievable with endocyclic heteroatoms. Studies in model systems[32,33] and the subsequent substitution of heteroatoms into cyclooctynes, such as diF-SNO-OCT and cyclononynes demonstrated the efficacy of this design principle.[20,21,26-28]

In parallel efforts, rate acceleration was pursued by increasing strain. In particular, benzannulation to give dibenzocyclooctyne (DIBO)[34] and dibenzoazacyclooctyne (DIBAC)[35,36] led to reaction rates comparable to those attained with electronic tuning and without compromise to reagent stability.

Limited success has been achieved in integrating electronic tuning with strain. The installation of remote heteroatoms has led to only incremental increases in reactivity[37] and compromised reagent stability.[25,36] Hence, reagents that harness both strategies are absent from the landscape. Accordingly, there is a need in the art for reagents that harness both strategies in order to further accelerate the rate of SPAAC and other 1,3-dipolar cycloaddition reactions.

SUMMARY

In one aspect, the present disclosure is directed to compounds of formula (I):

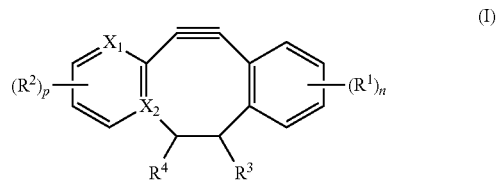

(I)

or a pharmaceutically acceptable salt thereof,
wherein:
$R^1$ and $R^2$ are, independently for each occurrence, F, Cl, Br, I, OTf, B(OH)$_2$, CN, NHR$^5$, NHS(O)$_2$R$^5$, OR$^5$, OS(O)$_2$R$^5$, SR$^5$, —CF$_3$, —C(O)OC$_{1-6}$ alkyl, —C(O)N(C$_{1-6}$ alkyl)$_2$, —C(O)R$^5$, S(O)$_2$R$^5$, NO$_2$, —C$_1$-6 alkyl, —C$_{1-6}$ alkenyl, or 5- to 10-membered heteroaryl substituted with 1, 2, 3, 4, or 5 R$^6$ groups, wherein the alkyl and alkenyl are optionally substituted with one or more R$^5$ group;
$R^3$ and $R^4$ are, independently for each occurrence, H or —C$_{1-6}$ alkyl;
$R^5$ is selected from H, —C$_{1-6}$-alkyl, —CF$_3$, —C(O)$_{1-6}$ alkyl, or —C(O)N(C$_{1-6}$ alkyl)$_2$;
$R^6$ is selected from H, F, Cl, Br, I, OTf, CN, NH$_2$, OR$^5$, SR$^5$, —CF$_3$; —C(O)R$^5$, —C(O)OC$_{1-6}$ alkyl, NO$_2$, —C$_{1-6}$ alkyl;
n is 0, 1, or 2;
p is 0, 1, or 2; and
provided that when $X_1$ is N, $X_2$ is C; or when $X_1$ is CH, $X_2$ is N$^+$.

In some embodiments, the compound of formula (I) is a compound of formula (Ia):

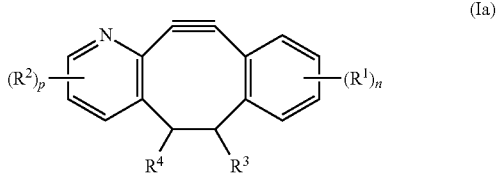

(Ia)

or a pharmaceutically acceptable salt thereof,
wherein:
$R^1$ and $R^2$ are, independently for each occurrence, F, Cl, Br, I, OTf, B(OH)$_2$, CN, NHR$^5$, NHS(O)$_2$R$^5$, OR$^5$, OS(O)$_2$R$^5$, —CF$_3$, —C(O)OC$_{1-6}$ alkyl, —C(O)N(C$_{1-6}$ alkyl)$_2$, —C(O)R$^5$, S(O)$_2$R$^5$, NO$_2$, —C$_{1-6}$ alkyl, —C$_{1-6}$ alkenyl, or 5- to 10-membered heteroaryl substituted with 1, 2, 3, 4, or 5 R$^6$ groups, optionally wherein the alkyl and alkenyl are substituted with one or more R$^5$ group;
$R^3$ and $R^4$ are, independently for each occurrence, H or —C$_{1-6}$ alkyl;
$R^5$ is selected from H, —C$_{1-6}$-alkyl, —CF$_3$, —C(O)OC$_{1-6}$ alkyl, or —C(O)N(C$_{1-6}$ alkyl)$_2$;
$R^6$ is selected from H, F, Cl, Br, I, OTf, CN, NH$_2$, OR$^5$, SR$^5$, —CF$_3$, —C(O)R$^5$, —C(O)OC$_{1-6}$ alkyl, NO$_2$, —C$_{1-6}$ alkyl;
n is 0, 1, or 2; and
p is 0, 1, or 2.

In some embodiments, $R^3$ and $R^4$ are H. In some embodiments, $R^1$ and $R^2$ are F, Cl, Br, I, OTf, or B(OH)$_2$. In some embodiments, $R^1$ and $R^2$ are Cl. In some embodiments, n is 1 and p is 0.

In some embodiments, the compound of formula (I) is a compound of formula (Ib):

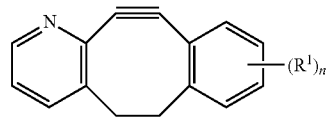
(Ib)

or a pharmaceutically acceptable salt thereof,
wherein $R^1$ is, independently for each occurrence, F, Cl, Br, I, OTf, B(OH)$_2$ or —C$_{1-6}$-alkyl; and
n is 0, 1, or 2.

In some embodiments, the compound of formula (I) is:

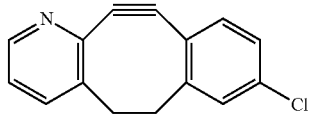 [SMILES: Clc1ccc2c(c1)CCc1cccnc1C#C2]

or a pharmaceutically acceptable salt thereof.

In further aspects, the present disclosure also provides a method of making a compound of formula (II):

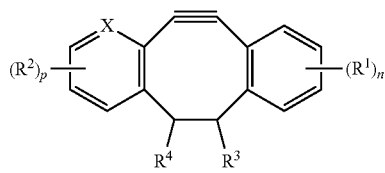
(II)

or a pharmaceutically accepted salt thereof,
wherein:
$R^1$ and $R^2$ are, independently for each occurrence, F, Cl, Br, I, OTf, B(OH)$_2$, CN, NHR$^5$, NHS(O)$_2$R$^5$, OR$^5$, OS(O)$_2$R$^5$, —CF$_3$, —C(O)OC$_{1-6}$ alkyl, —C(O)N(C$_{1-6}$ alkyl)$_2$, —C(O)R$^5$, S(O)$_2$R$^5$, NO$_2$, —C$_{1-6}$ alkyl, —C$_{1-6}$ alkenyl, or 5- to 10-membered heteroaryl substituted with 1, 2, 3, 4, or 5 R$^6$ groups, optionally wherein the alkyl and alkenyl are substituted with one or more R$^5$ group;
$R^3$ and $R^4$ are, independently for each occurrence, H or —C$_{1-6}$ alkyl;
$R^5$ is selected from H, —C$_{1-6}$-alkyl, —CF$_3$; —C(O)OC$_{1-6}$ alkyl, or —C(O)N(C$_{1-6}$ alkyl)$_2$;
$R^6$ is selected from H, F, Cl, Br, I, OTf, CN, NH$_2$, OR$^5$, SR$^5$, —CF$_3$, —C(O)R$^5$, —C(O)OC$_{1-6}$ alkyl, NO$_2$, —C$_{1-6}$ alkyl;
n is 0, 1, or 2;
p is 0, 1, or 2; and X is CH or N;
wherein the process comprises:
(A) combining a compound of formula (III):

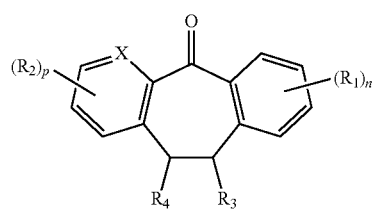
(III)

with a compound of formula (IV)

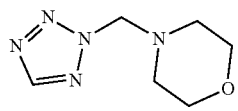
(IV)

and a non-nucleophilic base to provide the compound of formula (V):

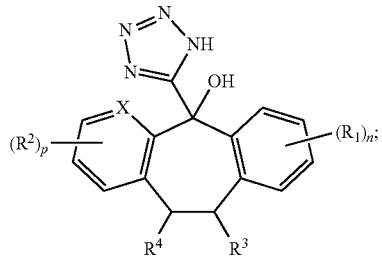
(V)

and
(B) combining the compound of formula (V) with a carbodiimide to provide the compound of formula (II).

In some embodiments, the compound of formula (II), has a structure according to formula (IIa):

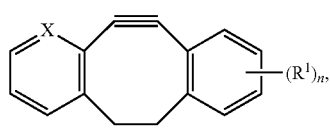
(IIa)

wherein $R^1$ is, independently for each occurrence, F, Cl, Br, I, OTf, B(OH)$_2$ or —C$_{1-6}$-alkyl;
n is 0, 1, or 2; and
X is CH or N.

In some embodiments, the compound of formula (II), has a structure selected from the group consisting of:

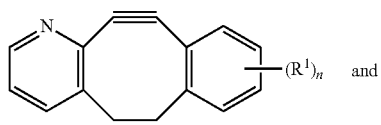 and

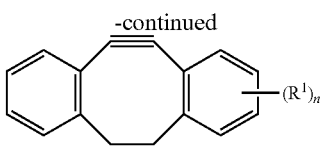

wherein $R^1$ is Cl, and
n is 0 or 1.

In some embodiments, the compound of formula (II), has a structure selected from the group consisting of:

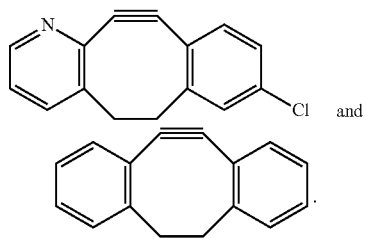

In some embodiments, the non-nucleophilic base is an alkyl lithium. In some embodiments, the non-nucleophilic base is lithium bis(trimethylsilyl)amide.

In some embodiments, the carbodiimide is 1-ethyl-3-(3-dimethylaminopropyl)carbodiimide (EDC).

In another aspect, the present disclosure also provides a process of making a compound of formula (VIa'):

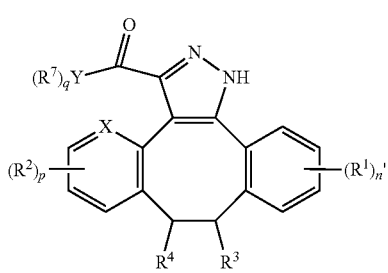

or regioisomer thereof,
wherein:
$R^1$ and $R^2$ are, independently for each occurrence, F, Cl, Br, I, OTf, B(OH)$_2$, CN, NHR$^5$, NHS(O)$_2$R$^5$, OR$^5$, OS(O)$_2$R$^5$, —CF$_3$, —C(O)OC$_{1-6}$ alkyl, —C(O)N(C$_{1-6}$ alkyl)$_2$, —C(O)R$^5$, S(O)$_2$R$^5$, NO$_2$, —C$_{1-6}$ alkyl, —C$_{1-6}$ alkenyl, or 5- to 10-membered heteroaryl substituted with 1, 2, 3, 4, or 5 R$^6$ groups, optionally wherein the alkyl and alkenyl are substituted with one or more R$^5$ group;
$R^3$ and $R^4$ are, independently for each occurrence, H or —C$_{1-6}$ alkyl;
$R^5$ is selected from H, —C$_{1-6}$-alkyl, —CF$_3$; —C(O)OC$_{1-6}$ alkyl, or —C(O)N(C$_{1-6}$ alkyl)$_2$;
$R^6$ is selected from H, F, Cl, Br, I, OTf, CN, NH$_2$, OR$^5$, SR$^5$, —CF$_3$, —C(O)R$^5$, —C(O)OC$_{1-6}$ alkyl, NO$_2$, —C$_{1-6}$ alkyl;
$R^7$ is C$_{1-6}$ alkyl optionally substituted with one or more C$_{6-10}$ aryl or 5- to 10-membered heteroaryl;
n is 0, 1, or 2;
p is 0, 1, or 2;
q is 1 or 2;
X is CH or N; and Y is O or NH;
wherein the process comprises combining a compound of formula (II):

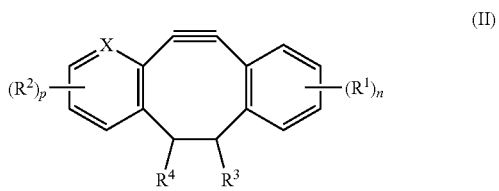

with a compound of formula (VIIa)

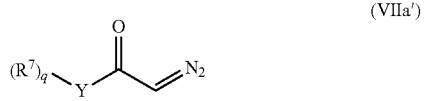

wherein:
$R^7$ is C$_{1-6}$ alkyl optionally substituted with one or more C$_{6-10}$ aryl or 5- to 10-membered heteroaryl; and
Y is O or NH;
to provide the compound of formula (VIa').

In some embodiments, the compound of formula (VIIa) is selected from the group consisting of:

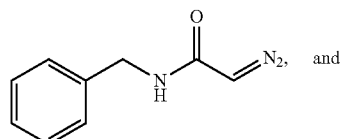

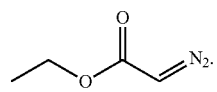

In some embodiments, the compound of formula (II) has a structure according to formula (IIa):

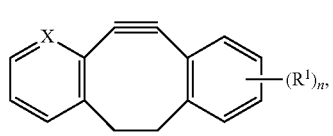

wherein $R^1$ is, independently for each occurrence, F, Cl, Br, I, OTf, B(OH)$_2$ or —C$_{1-6}$-alkyl;
n is 0, 1, or 2; and
X is CH or N.

In some embodiments, the compound of formula (II), has a structure selected from the group consisting of:

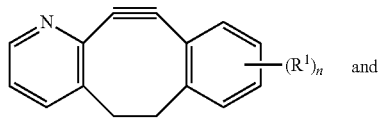

-continued

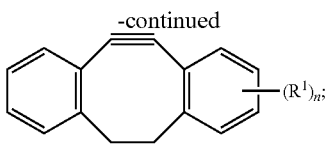

wherein R¹ is Cl; and
n is 0 or 1.

In some embodiments, the compound of formula (II), has a structure selected from the group consisting of:

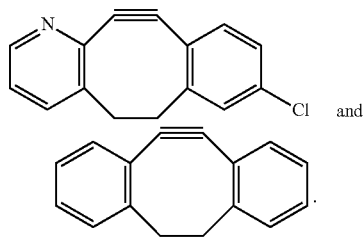

In another aspect, the present disclosure also provides a process of making a compound of formula (VIb'):

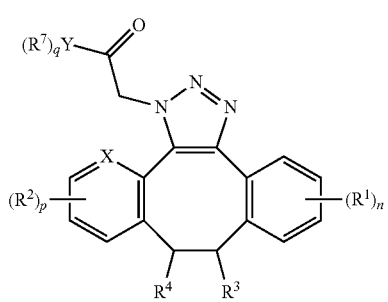

or regioisomer thereof,
wherein:

R¹ and R² are, independently for each occurrence, F, Cl, Br, I, OTf, B(OH)$_2$, CN, NHR⁵, NHS(O)$_2$R⁵, OR⁵, OS(O)$_2$R⁵, —CF$_3$, —C(O)OC$_{1-6}$ alkyl, —C(O)N(C$_{1-6}$ alkyl)$_2$, —C(O)R⁵, S(O)$_2$R⁵, NO$_2$, —C$_{1-6}$ alkyl, —C$_{1-6}$ alkenyl, or 5- to 10-membered heteroaryl substituted with 1, 2, 3, 4, or 5 R⁶ groups, wherein the alkyl and alkenyl are optionally substituted with one or more R⁵ group;

R³ and R⁴ are, independently for each occurrence, H or —C$_{1-6}$ alkyl;

R⁵ is selected from H, —C$_{1-6}$-alkyl, —CF$_3$, —C(O)CO$_{1-6}$ alkyl, or —C(O)N(C$_{1-6}$ alkyl)$_2$;

R⁶ is selected from H, F, Cl, Br, I, OTf, CN, NH$_2$, OR⁵, SR⁵, —CF$_3$, —C(O)R⁵, —C(O)OC$_{1-6}$ alkyl, NO$_2$, —C$_{1-6}$ alkyl;

R⁷ is C$_{1-6}$ alkyl optionally substituted with one or more C$_{6-10}$ aryl or 5- to 10-membered heteroaryl;

n is 0, 1, or 2;
p is 0, 1, or 2;
q is 1 or 2;
X is CH or N; and
Y is O or NH;

wherein the process comprises combining a compound of formula (II):

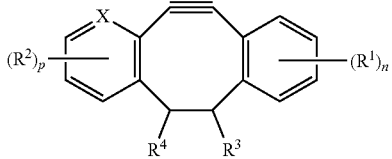

with a compound of formula (VIIa)

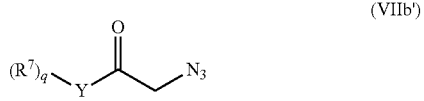

wherein:

R⁷ is C$_{1-6}$ alkyl optionally substituted with one or more C$_{6-10}$ aryl or 5- to 10-membered heteroaryl; and Y is O or NH;

to provide the compound of formula (VIb').

In some embodiments, the compound of formula (VIIb) is selected from the group consisting of:

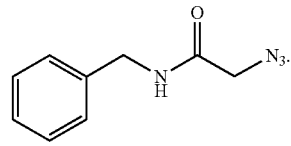 [SMILES: [N-]=[N+]=NCC(=O)NCc1ccccc1]

In some embodiments, the compound of formula (II) has a structure according to formula (IIa):

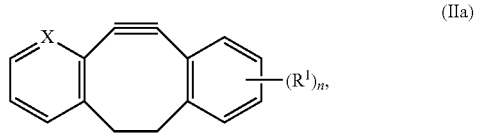

wherein R¹ is, independently for each occurrence, F, Cl, Br, I, OTf, B(OH)$_2$ or —C$_{1-6}$-alkyl;

n is 0, 1, or 2; and
X is CH or N.

In some embodiments, the compound of formula (II), has a structure selected from the group consisting of:

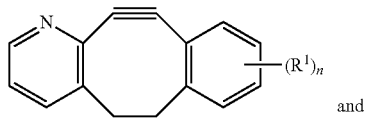

and

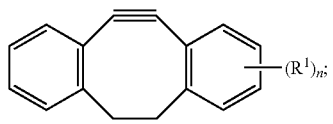

wherein R¹ is Cl; and
n is 0 or 1.

In some embodiments, the compound of formula (II), has a structure selected from the group consisting of:

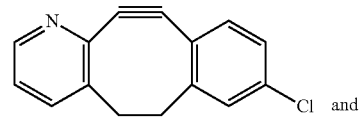

and

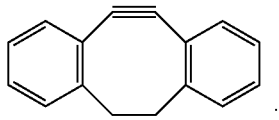

.

DETAILED DESCRIPTION

Figure 1:
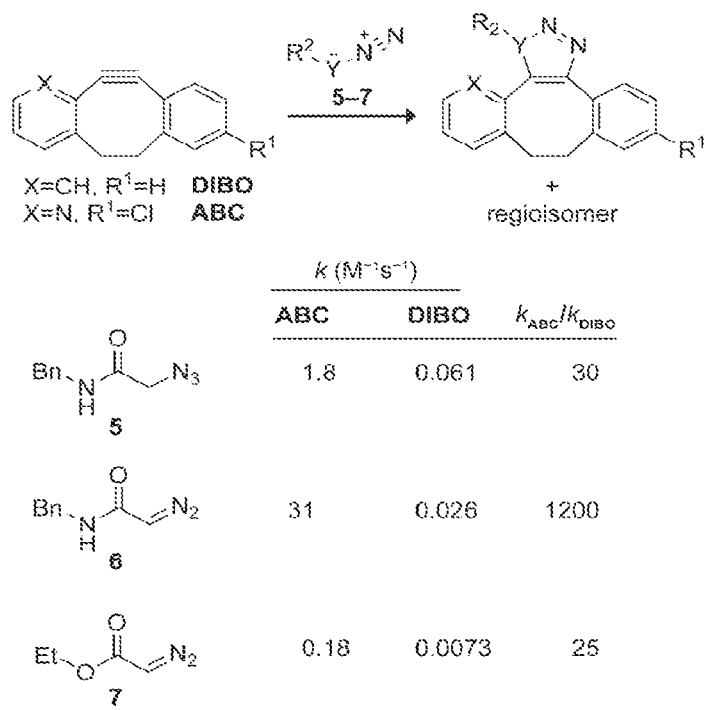
FIG. 1 shows second-order rate constants for the 1,3-dipolar cycloaddition of DIBO or compound 3 with dipoles (N-benzylazidoacetamide, N-benzyldiazoacetamide, and ethyl diazoacetate) in $CH_2Cl_2$. Values are the mean from triplicate experiments.

Provided herein are hybrid cyclooctyne compounds, or pharmaceutically acceptable salts thereof, that are useful reagents in 1,3-dipolar cycloaddition reactions, including strain-promoted azide—alkyne cycloaddition (SPAAC) reactions. This new class of cyclooctyne reagents provides a rate for cycloadditions that surpasses those of commercially available cyclooctyne reagents with negligible impact on stability in the presence of biological nucleophiles.

Definitions

Listed below are definitions of various terms used to describe the present disclosure. These definitions apply to the terms as they are used throughout this specification and claims, unless otherwise limited in specific instances, either individually or as part of a larger group.

Unless defined otherwise, all technical and scientific terms used herein generally have the same meaning as commonly understood by one of ordinary skill in the applicable art. Generally, the nomenclature used herein and the laboratory procedures in organic chemistry are those well-known and commonly employed in the art.

As used herein, the articles "a" and "an" refer to one or to more than one (i.e. to at least one) of the grammatical object of the article. Thus, for example, reference to "a solvent" includes a combination of two or more such solvents, reference to "a base" includes one or more bases, or mixtures of bases, and the like. Unless specifically stated or obvious from context, as used herein, the term "or" is understood to be inclusive and covers both "or" and "and." Furthermore, use of the term "including" as well as other forms, such as "include," "includes," and "included," is not limiting.

As used in the specification and in the claims, the terms "comprise(s)," "include(s)," "having," "has," "can," "contain(s)," and variants thereof, as used herein, are intended to be open-ended transitional phrases, terms, or words that require the presence of the named ingredients/steps and permit the presence of other ingredients/steps.

The term "alkyl" refers to a straight- or branched-chain alkyl group having the indicated number of carbon atoms. Examples of alkyl groups include methyl, ethyl, n-propyl, isopropyl, butyl, isobutyl, sec-butyl, tert-butyl, pentyl, isopentyl, tert-pentyl, hexyl, and isohexyl. The term $C_{1-4}$ alkyl as used here refers to a straight- or branched-chain alkyl group having from 1 to 4 carbon atoms in the chain. The term $C_{1-6}$ alkyl as used here refers to a straight- or branched-chain alkyl group having from 1 to 6 carbon atoms in the chain.

The term "aryl," unless otherwise stated," refers to a polyunsaturated, aromatic, hydrocarbon group which can be a single ring or multiple rings (up to three rings) which are fused together or linked covalently. Examples of aryl groups include phenyl, naphthyl, and anthracenyl.

The term "heteroaryl" refers to a monocyclic or bicyclic aryl ring system which contains carbon atoms and from 1 to 5 heteroatoms independently selected from the group consisting of N, O, and S. Included within the term heteroaryl are aromatic rings of 5 or 6 members wherein the ring consists of carbon atoms and has at least one heteroatom member. Examples of heteroaryl groups include furyl, thienyl, pyrrolyl, oxazolyl, thiazolyl, imidazolyl, pyrazolyl, oxazolyl, thiazolyl, oxadiazolyl, triazolyl, thiadiazolyl, pyridinyl, pyridazinyl, pyrimidinyl, pyrazinyl, indolyl, isoindolyl, benzofuryl, benzothienyl, indazolyl, benzimidazolyl, benzothiazolyl, benzoxazolyl, benzisoxazolyl, benzothiadiazolyl, benzotriazolyl, quinolinyl, isoquinolinyl and quinazolinyl. Unless otherwise noted, the heteroaryl is attached to its pendant group at any heteroatom or carbon atom that results in a stable structure.

The term "cyano" refers to the group —CN.

The terms "halo" or "halogen" represent chloro, fluoro, bromo, or iodo.

The term "substituted" means that the specified group or moiety bears one or more substituents. The term "unsubstituted" means that the specified group bears no substituents.

The term "optionally substituted" means that the specified group is unsubstituted or substituted by one or more substituents. Where the term "substituted" is used to describe a structural system, the substitution is meant to occur at any valency-allowed position on the system. In cases where a specified moiety or group is not expressly noted as being optionally substituted or substituted with any specified substituent, it is understood that such a moiety or group is intended to be unsubstituted.

To provide a more concise description, some of the quantitative expressions given herein are not qualified with the term "about". It is understood that, whether the term "about" is used explicitly or not, every quantity given herein is meant to refer to the actual given value, and it is also meant to refer to the approximation to such given value that would reasonably be inferred based on the ordinary skill in the art, including equivalents and approximations due to the experimental and/or measurement conditions for such given value. Whenever a yield is given as a percentage, such yield refers to a mass of the entity for which the yield is given with respect to the maximum amount of the same entity that could be obtained under the particular stoichiometric conditions. Concentrations that are given as percentages refer to mass ratios, unless indicated differently.

Any formula given herein is intended to represent compounds having structures depicted by the structural formula as well as certain variations or forms. In particular, compounds of any formula given herein may have asymmetric centers and therefore exist in different enantiomeric forms. All optical isomers of the compounds of the general formula, and mixtures thereof, are considered within the scope of the formula. Thus, any formula given herein is intended to represent a racemate, one or more enantiomeric forms, one or more diastereomeric forms, one or more atropisomeric forms, and mixtures thereof. Furthermore, certain structures may exist as geometric isomers (i.e., cis and trans isomers), as tautomers, or as atropisomers.

It is also to be understood that compounds that have the same molecular formula but differ in the nature or sequence of bonding of their atoms or the arrangement of their atoms in space are termed "isomers."

Stereoisomers that are not mirror images of one another are termed "diastereomers" and those that are non-superimposable mirror images of each other are termed "enantiomers." When a compound has an asymmetric center, for example, it is bonded to four different groups, and a pair of enantiomers is possible. An enantiomer can be characterized by the absolute configuration of its asymmetric center and is described by the R-and S-sequencing rules of Cahn and Prelog, or by the manner in which the molecule rotates the plane of polarized light and designated as dextrorotatory or levorotatory (i.e., as (+)- or (−)-isomers respectively). A chiral compound can exist as either an individual enantiomer or as a mixture thereof. A mixture containing equal proportions of the enantiomers is called a "racemic mixture."

"Tautomers" refer to compounds that are interchangeable forms of a particular compound structure, and that vary in the displacement of hydrogen atoms and electrons. Thus, two structures may be in equilibrium through the movement of π electrons and an atom (usually H). For example, enols and ketones are tautomers because they are rapidly interconverted by treatment with either acid or base. Another example of tautomerism is the aci- and nitro- forms of phenyl nitromethane, that are likewise formed by treatment with acid or base.

Tautomeric forms may be relevant to the attainment of the optimal chemical reactivity and biological activity of a compound of interest.

The compounds of the present disclosure may possess one or more asymmetric centers; such compounds can therefore be produced as individual (R)- or (S)-stereoisomers or as mixtures thereof.

Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art.

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the present disclosure include isotopes of hydrogen, carbon, nitrogen, oxygen, phosphorus, sulfur, fluorine, chlorine, and iodine such as $^{2}H$, $^{3}H$, $^{11}C$, $^{13}C$, $^{14}C$, $^{15}N$, $^{18}O$, $^{17}O$, $^{31}P$, $^{32}P$, $^{35}S$, $^{18}F$, $^{36}Cl$, $^{125}I$, respectively. Such isotopically labeled compounds are useful in metabolic studies (with $^{14}C$), reaction kinetic studies (with, for example deuterium (i.e., D or $^{2}H$); or tritium (i.e., T or $^{3}H$)), detection or imaging techniques such as positron emission tomography (PET) or single-photon emission computed tomography (SPECT) including drug or substrate tissue distribution assays, or in radioactive treatment of patients. In particular, an $^{18}F$ or $^{11}C$ labeled compound may be used for PET or SPECT studies. Further, substitution with heavier isotopes such as deuterium (i.e., $^{2}H$) may afford certain therapeutic advantages resulting from greater metabolic stability, for example increased in vivo half-life or reduced dosage requirements. Isotopically labeled compounds of the present disclosure and prodrugs thereof can generally be prepared by carrying out the procedures disclosed in the schemes or in the examples and preparations described below by substituting a readily available isotopically labeled reagent for a non-isotopically labeled reagent.

When referring to any formula given herein, the selection of a particular moiety from a list of possible species for a specified variable is not intended to define the same choice of the species for the variable appearing elsewhere. In other words, where a variable appears more than once, the choice of the species from a specified list is independent of the choice of the species for the same variable elsewhere in the formula, unless stated otherwise.

According to the foregoing interpretive considerations on assignments and nomenclature, it is understood that explicit reference herein to a set implies, where chemically meaningful and unless indicated otherwise, independent reference to embodiments of such set, and reference to each and every one of the possible embodiments of subsets of the set referred to explicitly.

The present disclosure includes also pharmaceutically acceptable salts of the compounds described herein.

The term "pharmaceutically acceptable" means approved or approvable by a regulatory agency of Federal or a state government or the corresponding agency in countries other than the United States, or that is listed in the U. S. Pharmacopoeia or other generally recognized pharmacopoeia for use in animals and humans.

A "pharmaceutically acceptable salt" is intended to mean a salt of a free acid or base of compounds represented by formula (I) that are non-toxic, biologically tolerable, or otherwise biologically suitable for administration to the subject. It should possess the desired pharmacological activity of the parent compound. See, generally, G. S. Paulekuhn, et al., "Trends in Active Pharmaceutical Ingredient Salt Selection based on Analysis of the Orange Book Database", *J. Med. Chem.*, 2007, 50:6665-72, S. M. Berge, et al., "Pharmaceutical Salts", *J. Pharm. Sci.*, 1977, 66:1-19, and *Handbook of Pharmaceutical Salts, Properties, Selection, and Use*, Stahl and Wermuth, Eds., Wiley-VCH and VHCA, Zurich, 2002. Examples of pharmaceutically acceptable salts are those that are pharmacologically effective and suitable for contact with the tissues of patients without undue toxicity, irritation, or allergic response. A compound of formula (I) may possess a sufficiently acidic group, a sufficiently basic group, or both types of functional groups, and accordingly react with a number of inorganic or organic bases, and inorganic and organic acids, to form a pharmaceutically acceptable salt.

Hybrid Cyclooctyne Compounds

Provided herein are dibenzocyclooctyne compounds, or pharmaceutically acceptable salts thereof.

Thus, in one aspect, provided herein is are compounds of formula (I):

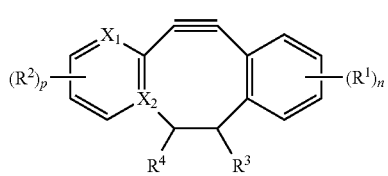

(I)

or a pharmaceutically acceptable salt thereof,
wherein:
$R^1$ and $R^2$ are, independently for each occurrence, F, Cl, Br, I, OTf, $B(OH)_2$, CN, $NHR^5$, $NHS(O)_2R^5$, $OR^5$, $OS(O)_2R^5$, $SR^5$, —$CF_3$, —$C(O)OC_{1-6}$ alkyl, —$C(O)N(C_{1-6}$ alkyl$)_2$, —$C(O)R^5$, $S(O)_2R^5$, $NO_2$, —$C_{1-6}$ alkyl, —$C_{1-6}$ alkenyl, or 5- to 10-membered heteroaryl substituted with 1, 2, 3, 4, or 5 $R^6$ groups, optionally wherein the alkyl and alkenyl are substituted with one or more $R^5$ group;
$R^3$ and $R^4$ are, independently for each occurrence, H or —$C_{1-6}$ alkyl;
$R^5$ is selected from H, —$C_{1-6}$-alkyl, —$CF_3$, —$C(O)OC_{1-6}$ alkyl, or —$C(O)N(C_{1-6}$ alkyl$)_2$;
$R^6$ is selected from H, F, Cl, Br, I, OTf, CN, $NH_2$, $OR^5$, $SR^5$, —$CF_3$; —$C(O)R^5$, —$C(O)OC_{1-6}$ alkyl, $NO_2$, —$C_{1-6}$ alkyl;
n is 0, 1, or 2;
p is 0, 1, or 2;
$X_1$ is N or CH; and
$X_2$ is $N^+$ or C;
provided that when $X_1$ is N, $X_2$ is C; or when $X_1$ is CH, $X_2$ is $N^+$.

In some embodiments, $R^1$ and $R^2$ are, independently for each occurrence, F, Cl, Br, I, OTf, $B(OH)_2$, —$C_{1-6}$ alkyl, or —$C_{1-6}$ alkenyl, optionally wherein the alkyl and alkenyl are substituted with one or more $R^5$ group.

In some embodiments, $R^1$ is F, Cl, Br, I, OTf, $B(OH)_2$ or —$C_{1-6}$-alkyl. In some embodiments, $R^1$ is F, Cl, Br, I, OTf, or $B(OH)_2$. In some embodiments, $R^1$ is F, Cl, Br, or I. In some embodiments, $R^1$ Cl or Br. In some embodiments, $R^1$ is Cl. In some embodiments, $R^1$ is Br.

In some embodiments, $R^2$ is F, Cl, Br, I, OTf, $B(OH)_2$ or —$C_{1-6}$-alkyl. In some embodiments, $R^2$ is F, Cl, Br, I, OTf, or $B(OH)_2$. In some embodiments, $R^2$ is F, Cl, Br, or I. In some embodiments, $R^2$ Cl or Br. In some embodiments, $R^2$ is Cl. In some embodiments, $R^2$ is Br.

In some embodiments, $R^3$ is H.
In some embodiments, $R^4$ is H.
In some embodiments, $R^3$ and $R^4$ are H.
In some embodiments, n is 1 and p is 0.
In some embodiments, n is 0 and p is 1.
In some embodiments, $X_1$ is N and $X_2$ is C. In some embodiments, $X_1$ is CH and $X_2$ is $N^+$.

In some embodiments, the compound of formula (I) is a compound of formula (Ia):

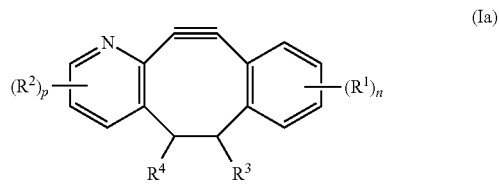

(Ia)

or a pharmaceutically acceptable salt thereof,
wherein:
$R^1$ and $R^2$ are, independently for each occurrence, F, Cl, Br, I, OTf, $B(OH)_2$, CN, $NHR^5$, $NHS(O)_2R^5$, $OR^5$, $OS(O)_2R^5$, $SR^5$, —$CF_3$, —$C(O)OC_{1-6}$ alkyl, —$C(O)N(C_{1-6}$ alkyl$)_2$, —$C(O)R^5$, $S(O)_2R^5$, $NO_2$, —$C_{1-6}$ alkyl, —$C_{1-6}$ alkenyl, or 5- to 10-membered heteroaryl substituted with 1, 2, 3, 4, or 5 $R^6$ groups, optionally wherein the alkyl and alkenyl are substituted with one or more $R^5$ group;
$R^3$ and $R^4$ are, independently for each occurrence, H or —$C_{1-6}$ alkyl;
$R^5$ is selected from H, -$C_{1-6}$-alkyl, —$CF_3$, —$C(O)OC_{1-6}$ alkyl, or —$C(O)N(C_{1-6}$ alkyl$)_2$;

$R^6$ is selected from H, F, Cl, Br, I, OTf, CN, $NH_2$, $OR^5$, $SR^5$, —$CF_3$, —$C(O)R^5$, —$C(O)OC_{1-6}$ alkyl, $NO_2$, —$C_{1-6}$ alkyl;

n is 0, 1, or 2; and p is 0, 1, or 2.

In some embodiments, $R^1$ and $R^2$ are, independently for each occurrence, F, Cl, Br, I, OTf, $B(OH)_2$, —$C_{1-6}$ alkyl, or —$C_{1-6}$ alkenyl, optionally wherein the alkyl and alkenyl are substituted with one or more $R^5$ group.

In some embodiments, $R^1$ is F, Cl, Br, I, OTf, $B(OH)_2$ or —$C_{1-6}$-alkyl. In some embodiments, $R^1$ is F, Cl, Br, I, OTf, or $B(OH)_2$. In some embodiments, $R^1$ is F, Cl, Br, or I. In some embodiments, $R^1$ Cl or Br. In some embodiments, $R^1$ is Cl. In some embodiments, $R^1$ is Br.

In some embodiments, $R^2$ is F, Cl, Br, I, OTf, $B(OH)_2$ or —$C_{1-6}$-alkyl. In some embodiments, $R^2$ is F, Cl, Br, I, OTf, or $B(OH)_2$. In some embodiments, $R^2$ is F, Cl, Br, or I. In some embodiments, $R^2$ Cl or Br. In some embodiments, $R^2$ is Cl. In some embodiments, $R^2$ is Br.

In some embodiments, $R^3$ is H.

In some embodiments, $R^4$ is H.

In some embodiments, $R^3$ and $R^4$ are H.

In some embodiments, n is 1 and p is 0.

In some embodiments, n is 0 and p is 1.

In some embodiments, the compound of formula (I) is a compound of formula (Ib):

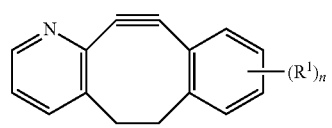

(Ib)

or a pharmaceutically acceptable salt thereof, wherein $R^1$ is, independently for each occurrence, F, Cl, Br, I, OTf, $B(OH)_2$ or —$C_{1-6}$-alkyl; and n is 0, 1, or 2.

In some embodiments, $R^1$ is F, Cl, Br, I, OTf, or $B(OH)_2$. In some embodiments, $R^1$ is F, Cl, Br, or I. In some embodiments, $R^1$ is Cl or Br. In some embodiments, $R^1$ is F. In some embodiments, $R^1$ is Cl. In some embodiments, $R^1$ is Br. In some embodiments, $R^1$ is I. In some embodiments, $R^1$ is OTf. In some embodiments, $R^1$ is $B(OH)_2$.

In some embodiments, n is 1.

In some embodiments, the compound of formula (I) is:

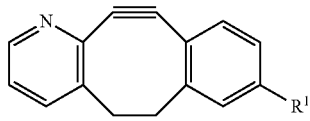

(Ic)

or a pharmaceutically acceptable salt thereof, wherein $R^1$ is, independently for each occurrence, F, Cl, Br, I, OTf, $B(OH)_2$ or —$C_{1-6}$-alkyl.

In some embodiments, $R^1$ is F, Cl, Br, I, OTf, or $B(OH)_2$. In some embodiments, $R^1$ is F, Cl, Br, or I. In some embodiments, $R^1$ is Cl or Br. In some embodiments, $R^1$ is F. In some embodiments, $R^1$ is Cl. In some embodiments, $R^1$ is Br. In some embodiments, $R^1$ is I. In some embodiments, $R^1$ is OTf. In some embodiments, $R^1$ is $B(OH)_2$.

In some embodiments, the compound of formula (I) is represented by one of the following structures, or a pharmaceutically acceptable salt thereof:

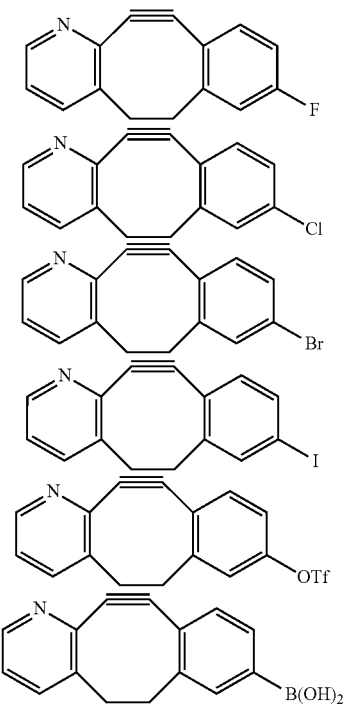

In some embodiments, the compound of formula (I) is:

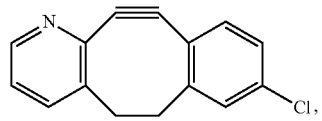

or a pharmaceutically acceptable salt thereof.

The instant disclosure also contemplates compounds having the following structures:

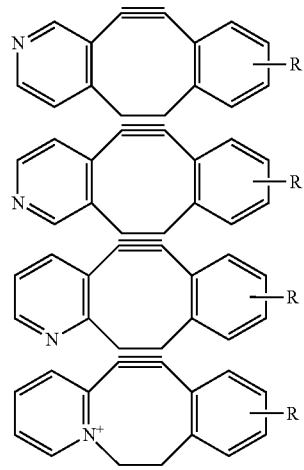

wherein R is H, F, Cl, Br, I, OTf, $B(OH)_2$ or —$C_{1-6}$-alkyl.

Preparation of Hybrid Cyclooctyne Compounds

The dibenzocyclooctyne compounds disclosed herein can be prepared by treating a dibenzo[7]annulen-5-one with N-morpholinomethyl-5-lithiotetrazole to produce the corresponding 5-hydroxyalkyl-1H-tetrazole, which undergoes a dehydrative fragmentation and rearrangement to produce the dibenzocyclooctyne compounds of the disclosure. This synthetic strategy can be used for the expedient synthesis of cyclooctyne compounds known in the art (e.g., DIBO) and has utility in the synthesis of other cycloalkynes as well.

Accordingly, in an aspect, the present disclosure also provides a method of making a compound of formula (II):

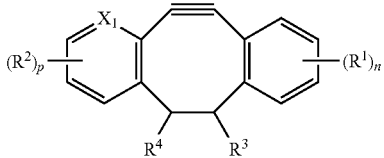

(II)

or a pharmaceutically accepted salt thereof,
wherein:
$R^1$ and $R^2$ are, independently for each occurrence, F, Cl, Br, I, OTf, B(OH)$_2$, CN, NHR$^5$, NHS(O)$_2$R$^5$, OR$^5$, OS(O)$_2$R$^5$, SR$^5$, —CF$_3$, —C(O)OC$_{1-6}$ alkyl, —C(O)N(C$_{1-6}$ alkyl)$_2$, —C(O)R$^5$, S(O)$_2$R$^5$, NO$_2$, —C$_{1-6}$ alkyl, —C$_{1-6}$ alkenyl, or 5- to 10-membered heteroaryl substituted with 1, 2, 3, 4, or 5 R$^6$ groups, optionally wherein the alkyl and alkenyl are substituted with one or more R$^5$ group;
$R^3$ and $R^4$ are, independently for each occurrence, H or —C$_{1-6}$ alkyl;
$R^5$ is selected from H, —C$_{1-6}$-alkyl, —CF$_3$; —C(O)OC$_{1-6}$ alkyl, or —C(O)N(C$_{1-6}$ alkyl)$_2$;
$R^6$ is selected from H, F, Cl, Br, I, OTf, CN, NH$_2$, OR$^5$, SR$^5$, —CF$_3$, —C(O)R$^5$, —C(O)OC$_{1-6}$ alkyl, NO$_2$, —C$_{1-6}$ alkyl;
n is 0, 1, or 2;
p is 0, 1, or 2; and
X is CH or N;
wherein the process comprises:
(A) combining a compound of formula (III):

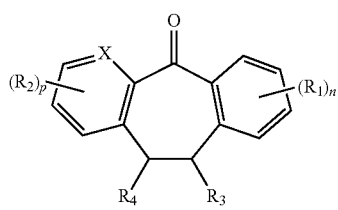

(III)

with a compound of formula (IV)

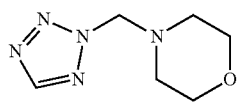

(IV)

and a non-nucleophilic base to provide the compound of formula (V):

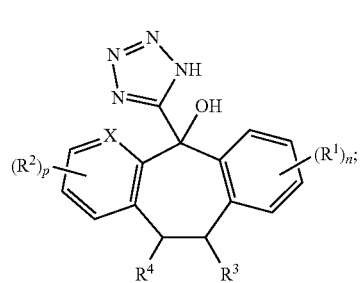

(V)

and (B) combining the compound of formula (V) with a carbodiimide to provide the compound of formula (II).

In some embodiments, $R^1$ and $R^2$ are, independently for each occurrence, F, Cl, Br, I, OTf, B(OH)$_2$, —C$_{1-6}$ alkyl, or —C$_{1-6}$ alkenyl, optionally wherein the alkyl and alkenyl are substituted with one or more R$^5$ group.

In some embodiments, $R^1$ is F, Cl, Br, I, OTf, B(OH)$_2$ or —C$_{1-6}$-alkyl. In some embodiments, $R^1$ is F, Cl, Br, I, OTf, or B(OH)$_2$. In some embodiments, $R^1$ is F, Cl, Br, or I. In some embodiments, $R^1$ Cl or Br. In some embodiments, $R^1$ is Cl. In some embodiments, $R^1$ is Br.

In some embodiments, $R^2$ is F, Cl, Br, I, OTf, B(OH)$_2$ or —C$_{1-6}$-alkyl. In some embodiments, $R^2$ is F, Cl, Br, I, OTf, or B(OH)$_2$. In some embodiments, $R^2$ is F, Cl, Br, or I. In some embodiments, $R^2$ Cl or Br. In some embodiments, $R^2$ is Cl. In some embodiments, $R^2$ is Br.

In some embodiments, $R^3$ is H.

In some embodiments, $R^4$ is H.

In some embodiments, $R^3$ and $R^4$ are H.

In some embodiments, n is 1 and p is 0.

In some embodiments, n is 0 and p is 1.

In some embodiments, the compound of formula (II), has a structure according to formula (IIa):

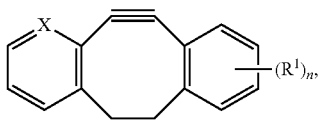

(IIa)

wherein $R^1$ is, independently for each occurrence, F, Cl, Br, I, OTf, B(OH)$_2$ or —C$_{1-6}$-alkyl;
n is 0, 1, or 2; and
X is CH or N.

In some embodiments, $R^1$ is F, Cl, Br, or I. In some embodiments, $R^1$ is Cl. In some embodiments, $R^1$ is Br. In some embodiments, $R^1$ is F. In some embodiments, $R^1$ is I. In some embodiments, $R^1$ is OTf. In some embodiments, $R^1$ is B(OH)$_2$.

In some embodiments, n is 0 or 1. In some embodiments, n is 0. In some embodiments, n is 1.

In some embodiments, X is CH. In some embodiments, X is N.

In some embodiments, the compound of formula (II), has a structure selected from the group consisting of:

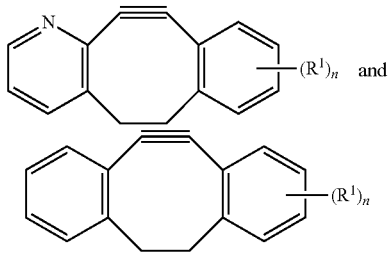 and wherein R¹ is Cl; and
n is 0 or 1.

In some embodiments, the compound of formula (II), has a structure selected from the group consisting of:

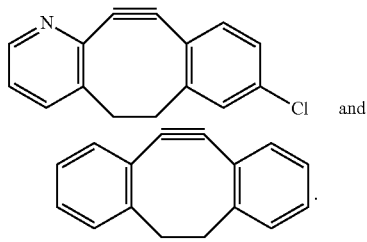

In some embodiments, the non-nucleophilic base comprises a carbon—lithium or a nitrogen-lithium bond. In some embodiments, the non-nucleophilic base is an alkyl lithium. In some embodiments, the non-nucleophilic base is methyllithium, butyllithium or tert-butyllithium. In some embodiments, the non-nucleophilic base comprises a nitrogen—lithium bond. In some embodiments, the non-nucleophilic base is lithium bis(trimethylsilyl)amide (LiHMDS), lithium diisopropylamide (LDA), or lithium tetramethylpiperidide (LiTMP). In some embodiments, the non-nucleophilic base is lithium bis(trimethylsilyl)amide (LiHDMS).

In some embodiments, step (A) is performed in a solvent. In some embodiments, the solvent is an organic solvent. By nonlimiting example, suitable solvents include dichloroethane, diethylether, diglyme, dimethylformamide, dimethyl sulfoxide, dioxane, methyl tert-butyl ether, methylene chloride, petroleum ether, tetrahydrofuran, and toluene. In some embodiments, the solvent is tetrahydrofuran.

In some embodiments, the carbodiimide is N,N'-dicyclohexylcarbodiimide (DCC), 1-ethyl-3-(3-dimethylaminopropyl)carbodiimide (EDC), N,N'-diisopropylcarbodiimide (DIC), or 1-cyclohexyl-(2-morpholinoethyl)carbodiimide (CMC). In some embodiments, the carbodiimide is 1-ethyl-3-(3-dimethylaminopropyl)carbodiimide (EDC). In some embodiments, the carbodiimide is 1-ethyl-3-(3-dimethylaminopropyl)carbodiimide hydrochloride.

In some embodiments, step (B) is performed in a solvent. In some embodiments, the solvent is an organic solvent. By nonlimiting example, suitable solvents include dichloroethane, diethylether, diglyme, dimethylformamide, dimethyl sulfoxide, dioxane, methyl tert-butyl ether, methylene chloride, petroleum ether, tetrahydrofuran, and toluene. In some embodiments, the solvent is tetrahydrofuran.

In some embodiments, step (B) comprises an alkylidene carbene rearrangement. In some embodiments, step (B) comprises in situ formation of a compound of formula (VI):

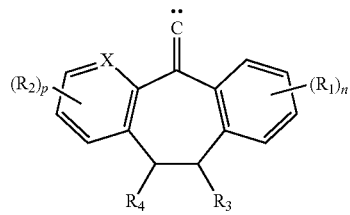

wherein $R^1$, $R^2$, $R^3$, $R^4$, n, p, and X are as defined hereinabove. In some embodiments, step (B) comprises an alkylidene carbene rearrangement of a compound of formula (VI).

The methods described herein provide a concise, two-step route to cyclooctyne compounds. While some cyclooctyne compounds useful as reagents in SPAAC reactions have been reported in the art, the reported synthetic protocols for preparing these compounds is generally laborious and can involve up to 11 steps. DIBO and DIBAC, for example, are synthesized in five or nine steps, respectively. Certain cyclooctynes along with the number of synthetic steps required for their preparation are disclosed in Dommerholt, J., et al. Strain-promoted 1,3-dipolar cycloaddition of cycloalkynes and organic azides *Top. Curr. Chem.* 2016, 374, 16, the entire contents of which are incorporated herein by reference. The methods of the present disclosure provide a significantly more efficient and cost-effective route toward cyclooctyne and cycloalkyne compounds that may be used as reagents in 1,3-dipolar cycloaddition reactions.

Alkylidene Carbene Rearrangements

The synthesis of a cyclic alkyne, such as the cyclooctynes disclosed herein, from a carbonyl compound via an alkylidene carbene is unknown (see, e.g., Habrant, et al., "Conversion of Carbonyl Compounds to Alkynes: General Overview and Recent Developments" *Chem. Soc. Rev.* 2010, 39:2007-17). Success was not anticipated because a R—C(O)—R' carbonyl group is bent but a R—C≡C—R' alkyne is linear. Thus, the conversion of a carbonyl group within a cyclic compound into an alkyne can lead to strain. The conversion of a compound of formula (V) to a compound of formula (II) proceeds via an alkylidene carbene intermediate. Accordingly, the disclosure also provides a method of making a compound of formula (II):

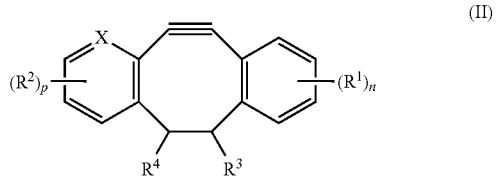

or a pharmaceutically accepted salt thereof,
wherein:
$R^1$ and $R^2$ are, independently for each occurrence, F, Cl, Br, I, OTf, B(OH)$_2$, CN, NHR$^5$, NHS(O)$_2$R$^5$, OR$^5$, OS(O)$_2$R$^5$, SR$^5$, —CF$_3$, —C(O)OC$_{1-6}$ alkyl, —C(O)N(C$_{1-6}$ alkyl)$_2$, —C(O)R$^5$, S(O)$_2$R$^5$, NO$_2$, —C$_{1-6}$ alkyl, —C$_{1-6}$ alkenyl, or 5- to 10-membered heteroaryl substituted with 1, 2, 3, 4, or 5 R$^6$ groups, optionally wherein the alkyl and alkenyl are substituted with one or more R$^5$ group;
$R^3$ and $R^4$ are, independently for each occurrence, H or —C$_{1-6}$ alkyl;

$R^5$ is selected from H, —$C_{1-6}$-alkyl, —$CF_3$; —$C(O)OC_{1-6}$ alkyl, or —$C(O)N(C_{1-6}$ alkyl$)_2$;
$R^6$ is selected from H, F, Cl, Br, I, OTf, CN, $NH_2$, $OR^5$, $SR^5$, —$CF_3$, —$C(O)R^5$, —$C(O)OC_{1-6}$ alkyl, $NO_2$, —$C_{1-6}$ alkyl;
n is 0, 1, or 2;
p is 0, 1, or 2; and
X is CH or N;
wherein the process comprises:
(A) in situ formation of a compound of formula (VI):

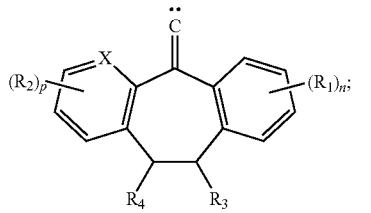

and
(B) an alkylidene carbene rearrangement of the compound of formula (VI) to provide the compound of formula (II).

In some embodiments, $R^1$ and $R^2$ are, independently for each occurrence, F, Cl, Br, I, OTf, $B(OH)_2$, —$C_{1-6}$ alkyl, or —$C_{1-6}$ alkenyl, optionally wherein the alkyl and alkenyl are substituted with one or more $R^5$ group.

In some embodiments, $R^1$ is F, Cl, Br, I, OTf, $B(OH)_2$ or —$C_{1-6}$-alkyl. In some embodiments, $R^1$ is F, Cl, Br, I, OTf, or $B(OH)_2$. In some embodiments, $R^1$ is F, Cl, Br, or I. In some embodiments, $R^1$ Cl or Br. In some embodiments, $R^1$ is Cl. In some embodiments, $R^1$ is Br.

In some embodiments, $R^2$ is F, Cl, Br, I, OTf, $B(OH)_2$ or —$C_{1-6}$-alkyl. In some embodiments, $R^2$ is F, Cl, Br, I, OTf, or $B(OH)_2$. In some embodiments, $R^2$ is F, Cl, Br, or I. In some embodiments, $R^2$ Cl or Br. In some embodiments, $R^2$ is Cl. In some embodiments, $R^2$ is Br.

In some embodiments, $R^3$ is H.
In some embodiments, $R^4$ is H.
In some embodiments, $R^3$ and $R^4$ are H.
In some embodiments, n is 1 and p is 0.
In some embodiments, n is 0 and p is 1.
In some embodiments, the compound of formula (II), has a structure according to formula (IIa):

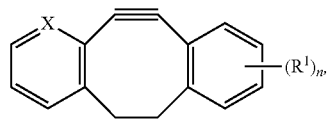

wherein $R^1$ is, independently for each occurrence, F, Cl, Br, I, OTf, $B(OH)_2$ or —$C_{1-6}$-alkyl;
n is 0, 1, or 2; and
X is CH or N.
In some embodiments, $R^1$ is F, Cl, Br, or I. In some embodiments, $R^1$ is Cl. In some embodiments, $R^1$ is Br. In some embodiments, $R^1$ is F. In some embodiments, $R^1$ is I. In some embodiments, $R^1$ is OTf. In some embodiments, $R^1$ is $B(OH)_2$.

In some embodiments, n is 0 or 1. In some embodiments, n is 0. In some embodiments, n is 1.

In some embodiments, X is CH. In some embodiments, X is N.

In some embodiments, the compound of formula (II), has a structure selected from the group consisting of:

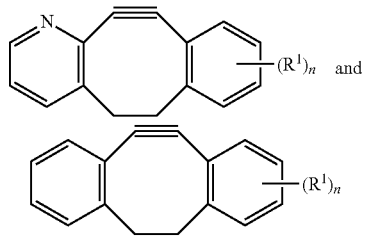

wherein $R^1$ is Cl; and
n is 0 or 1.
In some embodiments, the compound of formula (II), has a structure selected from the group consisting of:

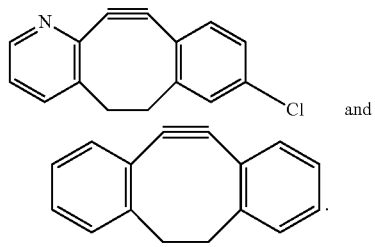

In situ formation of the compound of formula (VI) may occur via any protocol known in the art or described herein. For example, the compound of formula (VI) may be formed by combining a compound of formula (V) with a carbodiimide, as described hereinabove. Alternately, the compound of formula (VI) may be formed using other methods, such as the reaction of a ketone with trimethylsilyl diazomethane and a strong base, the reaction of a ketone with a dialkyl (diazomethyl)phosphonate and a strong base (the Seyferth-Gilbert homologation), or the treatment of halogenated alkenes with a strong base.

Accordingly, in some embodiments, the compound of formula (VI) is formed by combining a compound of formula (V) with a carbodiimide.

In some embodiments, the compound of formula (VI) is formed via the reaction of a ketone (i.e., a compound of formula (III)) with trimethylsilyl diazomethane and a strong base. In this method, a ketone, trimethylsilyl diazomethane, and a strong base are dissolved in an organic solvent and stirred to furnish the alkylidene carbene, which rearranges to form an alkyne. An example of this method for alkylidene carbene generation can be found in Dale, et al., "Systematic Evaluation of 1,2-Migratory Aptitude in Alkylidene Carbenes", *J. Am. Chem. Soc.*, 2021, 143:2097-107, the entire contents of which are incorporated herein by reference.

In some embodiments, the compound of formula (VI) is formed via the reaction of a ketone (i.e., a compound of formula (III)) with a dialkyl (diazomethyl)phosphonate and a strong base (via the Seyferth—Gilbert homologation). In this method, a ketone, a dialkyl (diazomethyl)phosphonate, and a strong base are dissolved in an organic solvent, and the resulting solution is stirred at low temperature to furnish the alkylidene carbene, which rearranges to an alkyne. An example of this method for alkylidene carbene generation can be found in Gilbert and Weerasooriya, "Diazoethenes: Their Attempted Synthesis from Aldehydes and Aromatic Ketones by Way of the Horner-Emmons Modification of the Wittig Reaction. A Facile Synthesis of Alkynes", *J. Org. Chem.* 1982, 47:1837-45, the entire contents of which are incorporated herein by reference.

In some embodiments, the alkylidene carbene is formed via the treatment of a dihalogenated alkene with an organolithium species. In this method, a geminally dihalogenated alkene is treated with an organolithium species in an organic solvent to furnish the alkylidene carbene, which rearranges to an alkyne. An example of this method for alkylidene carbene generation can be found in Köbrich, et al., "Chemistry of Stable α-Halogenoorganolithium Compounds and the Mechanism of Carbenoid Reactions", *Angew. Chem., Int. Ed.* 1967, 6:41-52, the entire contents of which are incorporated herein by reference.

1,3-Dipolar Cycloaddition

The dibenzocyclooctynes disclosed herein are capable of undergoing 1,3-dipolar cycloaddition reactions with dipolar reagents. The dibenzocyclooctynes are useful as reagents in strain-promoted azide-alkyne cycloaddition (SPAAC) reactions. Thus, the dibenzocyclooctynes of the present disclosure can react with azides to provide triazole-containing products. The azides may be unsubstituted or substituted. The azides may, for example, be conjugated to a small molecule, a carbohydrate, a peptide, a protein, or any such molecule contemplated in the art. Additionally, the dibenzocyclooctynes of the present disclosure can react with diazo compounds to provide pyrazole-containing products. The diazo compounds are stabilized via conjugation to an electron withdrawing group. For example, the diazo compounds may be α-diazoketones, α-diazoesters, or α-diazoamides. The diazo compounds may be further conjugated to, for example, a small molecule, a carbohydrate, a peptide, a protein, or any such molecule contemplated in the art. The dibenzocyclooctynes of the present disclosure may be derivatized prior to the cycloaddition reaction. The dibenzocyclooctynes include a handle for functionalization (e.g., a halogen) that can be substituted through well-established chemistry (e.g., a cross-coupling reaction) to introduce a substituent or domain to the dibenzocyclooctyne core.

Accordingly, in another aspect, the present disclosure also provides a process of making a compound of formula (VIa):

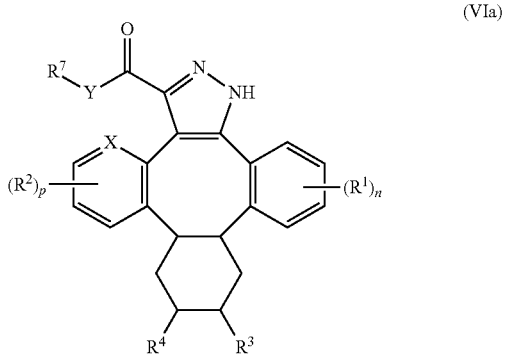

(VIa)

or regioisomer thereof,
wherein:
$R^1$ and $R^2$ are, independently for each occurrence, F, Cl, Br, I, OTf, $B(OH)_2$, CN, $NHR^5$, $NHS(O)_2R^5$, $OR^5$, $OS(O)_2R^5$, $SR^5$, $-CF_3$, $-C(O)OC_{1-6}$ alkyl, $-C(O)N(C_{1-6}$ alkyl$)_2$, $-C(O)R^5$, $S(O)_2R^5$, $NO_2$, $-C_{1-6}$ alkyl, $-C_{1-6}$ alkenyl, or 5- to 10-membered heteroaryl substituted with 1, 2, 3, 4, or 5 $R^6$ groups, optionally wherein the alkyl and alkenyl are substituted with one or more $R^5$ group;

$R^3$ and $R^4$ are, independently for each occurrence, H or $-C_{1-6}$ alkyl;

$R^5$ is selected from H, $-C_{1-6}$-alkyl, $-CF_3$; $-C(O)OC_{1-6}$ alkyl, or $-C(O)N(C_{1-6}$ alkyl$)_2$;

$R^6$ is selected from H, F, Cl, Br, I, OTf, CN, $NH_2$, $OR^5$, $SR^5$, $-CF_3$, $-C(O)R^5$, $-C(O)OC_{1-6}$ alkyl, $NO_2$, $-C_{1-6}$ alkyl;

$R^7$ is $C_{1-6}$ alkyl optionally substituted with one or more $C_{6-10}$ aryl or 5- to 10-membered heteroaryl;

n is 0, 1, or 2;

p is 0, 1, or 2;

X is CH or N;

Y is O or NH; and wherein the process comprises combining a compound of formula (II):

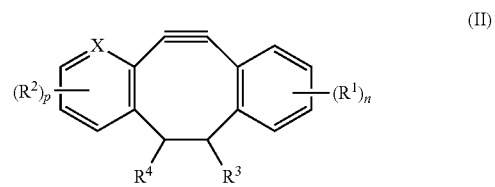

(II)

with a compound of formula (VIIa)

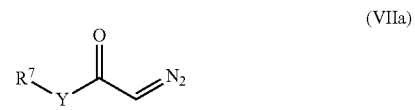

(VIIa)

to provide the compound of formula (VIa).

In some embodiments, the compound of formula (VIIa) is selected from the group consisting of:

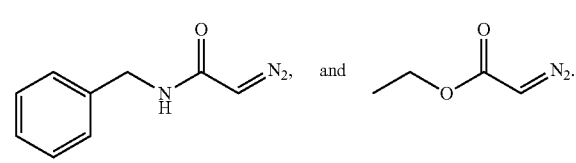

In some embodiments, the compound of formula (II) has a structure according to formula (IIa):

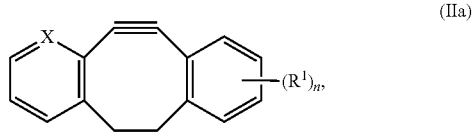

(IIa)

wherein $R^1$ is, independently for each occurrence, F, Cl, Br, I, OTf, $B(OH)_2$ or $-C_{1-6}$-alkyl;

n is 0, 1, or 2; and

X is CH or N.

In some embodiments, the compound of formula (II), has a structure selected from the group consisting of:

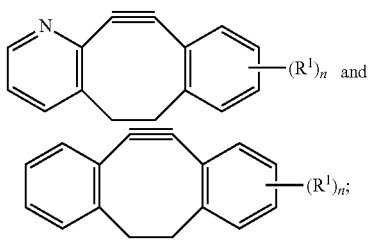

wherein R$^1$ is Cl; and
n is 0 or 1.

In some embodiments, the compound of formula (II), has a structure selected from the group consisting of:

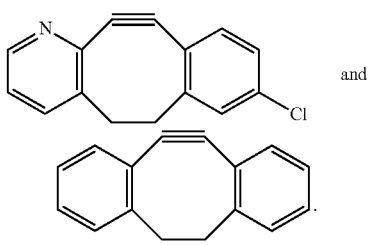

In some embodiments, the process is performed in a solvent. In some embodiments, the process is performed in an organic solvent. In some embodiments, the process is performed in methylene chloride.

In another aspect, the present disclosure also provides a process of making a compound of formula (VIb):

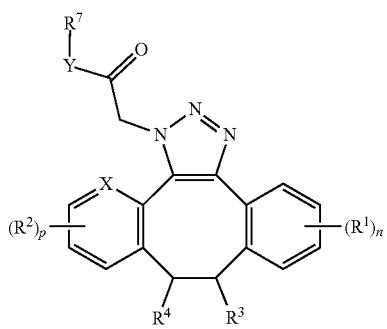

or regioisomer thereof,
wherein:

R$^1$ and R$^2$ are, independently for each occurrence, F, Cl, Br, I, OTf, B(OH)$_2$, CN, NHR$^5$, NHS(O)$_2$R$^5$, OR$^5$, OS(O)$_2$R$^5$, SR$^5$, —CF$_3$, —C(O)OC$_{1-6}$ alkyl, —C(O)N(C$_{1-6}$ alkyl)$_2$, —C(O)R$^5$, S(O)$_2$R$^5$, NO$_2$, —C$_{1-6}$ alkyl, —C$_{1-6}$ alkenyl, or 5- to 10-membered heteroaryl substituted with 1, 2, 3, 4, or 5 R$^6$ groups, optionally wherein the alkyl and alkenyl are substituted with one or more R$^5$ group;

R$^3$ and R$^4$ are, independently for each occurrence, H or —C$_{1-6}$ alkyl;

R$^5$ is selected from H, —C$_{1-6}$-alkyl, —CF$_3$; —C(O)OC$_{1-6}$ alkyl, or —C(O)N(C$_{1-6}$ alkyl)$_2$;

R$^6$ is selected from H, F, Cl, Br, I, OTf, CN, NH$_2$, OR$^5$, SR$^5$, —CF$_3$, —C(O)R$^5$, —C(O)OC$_{1-6}$ alkyl, NO$_2$, —C$_{1-6}$ alkyl;

R$^7$ is C$_{1-6}$ alkyl optionally substituted with one or more C$_{6-10}$ aryl or 5- to 10-membered heteroaryl;

n is 0, 1, or 2;
p is 0, 1, or 2;
X is CH or N;
Y is O or NH; and wherein the process comprises combining a compound of formula (II):

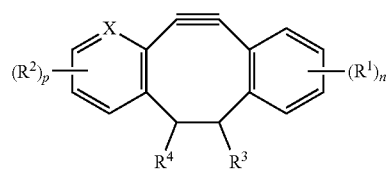

with a compound of formula (VIIa)

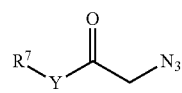

(VIIb)

to provide the compound of formula (VIb).

In some embodiments, the compound of formula (VIIb) is selected from the group consisting of:

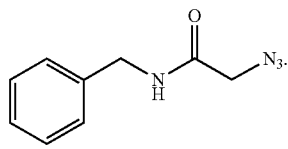 [SMILES: [N-]=[N+]=NCC(=O)NCc1ccccc1]

In some embodiments, the compound of formula (II) has a structure according to formula (IIa):

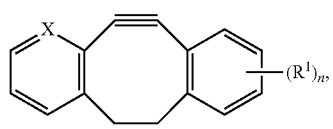

(IIa)

wherein R$^1$ is, independently for each occurrence, F, Cl, Br, I, OTf, B(OH)$_2$ or —C$_{1-6}$-alkyl;

n is 0, 1, or 2; and
X is CH or N.

In some embodiments, the compound of formula (II), has a structure selected from the group consisting of:

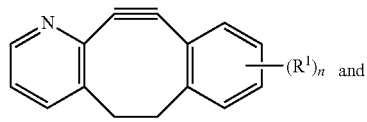

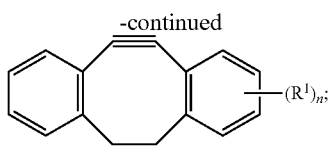

wherein R¹ is Cl; and
n is 0 or 1.

In some embodiments, the compound of formula (II), has a structure selected from the group consisting of:

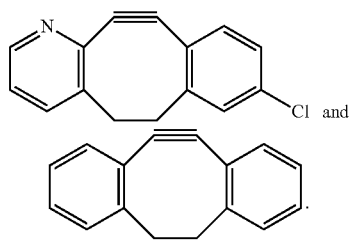

In some embodiments, the process is performed in a solvent. In some embodiments, the process is performed in an organic solvent. In some embodiments, the process is performed in methylene chloride.

EXAMPLES

The following examples are merely illustrative and are not intended to limit the disclosure to the materials, conditions, or process parameters set forth therein.

Example 1—Computational Design of Dibenzocyclooctynes

Gaussian 16 was used to identify modifications of the dibenzocyclooctyne scaffold that would accelerate its 1,3-dipolar cycloaddition with azides and diazo compounds. 1,3-dipolar cycloaddition reactions of both N-methylazido-acetamide (1) and N-methyldiazoacetamide (2) with DIBO and DIBAC, as well as a series of constitutional isomers of DIBAC (1-ABC to 6-ABC), were modeled (Table 1). Geometry optimizations were performed at the M06-2X level of theory (including the IEFPCM dielectric continuum solvent model for either $CH_2Cl_2$ or water, with UFF radii) or the B97D/6-311+G(d,p) level of theory (including the CPCM solvation model for either $CH_2Cl_2$ or water). Frequency calculations were performed to confirm stationary points as minima or first-order saddle points. All ΔE and $\Delta^{555}$ values include zero-point corrections. For previous reports benchmarking the methods utilized.

The installation of a nitrogen in DIBO was observed to unexpectedly lower the predicted energy barriers for cycloaddition with N-methyl azidoacetamide and N-methyl diazoacetamide. Smaller differences in activation energies (ΔE‡) and free energies of activation (ΔG‡) were observed for 3-, 4-, and 5-ABC in their reactions with dipoles N-methyl azidoacetamide and N-methyl diazoacetamide. In contrast, 2-ABC and 6-ABC were predicted to be more reactive than the other constitutional isomers. Notably, 2-ABC and 6-ABC contain a propargylic C—N bond that enables a direct interaction between the alkyne π-bond and the C—N antibonding orbital ($\sigma^*_{C-N}$).

TABLE 1

Effect of nitrogen placement in dibenzocyclooctynes on ΔE‡ and ΔG‡.

| | | | 1 | | 2 | |
|---|---|---|---|---|---|---|
| | | | syn TS | anti TS | syn TS | anti TS |
| DIBO | | ΔE‡: | 9.0 | anti TS | 10.6 | anti TS |
| | | ΔG‡: | 23.9 | — | 23.7 | — |
| CH₂→NH | | | | | | |
| DIBAC | | ΔE‡: | 8.7 | 7.7 | 10.1 | 8.9 |
| | | ΔG‡: | 23.6 | 22.6 | 23.3 | 22.1 |
| condtitutional isomers | | | | | | |
| 2-ABC | | ΔE‡: | 8.6 | 9.3 | 6.2 | 10.6 |
| | | ΔG‡: | 22.2 | 24.5 | 19.5 | 23.7 |
| 3-ABC | | ΔE‡: | 9.0 | 8.4 | 10.0 | 9.8 |
| | | ΔG‡: | 23.5 | 23.1 | 22.8 | 22.8 |

TABLE 1-continued

Effect of nitrogen placement in dibenzocyclooctynes on $\Delta E^{\ddagger}$ and $\Delta G^{\ddagger}$.

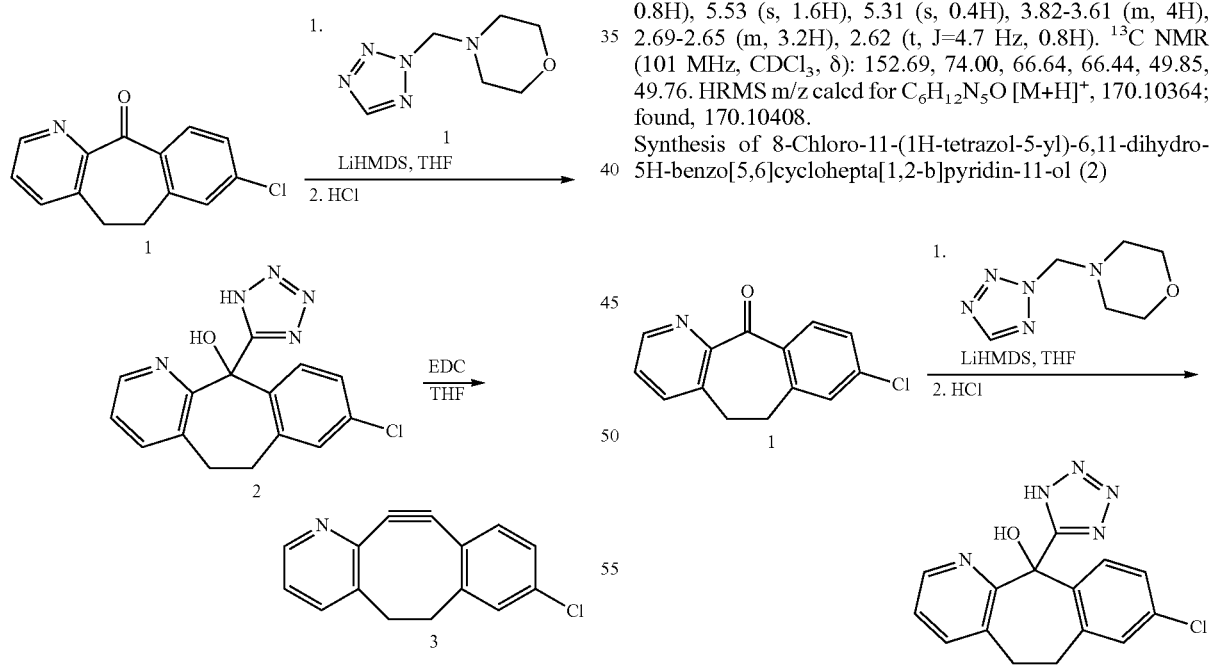

|  |  |  | 1 | | 2 | |
|---|---|---|---|---|---|---|
|  |  |  | syn TS | anti TS | syn TS | anti TS |
| 4-ABC |  | $\Delta E^{\ddagger}$: | 9.0 | 8.3 | 9.9 | 9.8 |
|  |  | $\Delta G^{\ddagger}$: | 23.7 | 23.0 | 22.7 | 22.8 |
| 5-ABC |  | $\Delta E^{\ddagger}$: | 9.2 | 8.5 | 10.3 | 10.0 |
|  |  | $\Delta G^{\ddagger}$: | 23.9 | 23.0 | 23.2 | 23.2 |
| 6-ABC |  | $\Delta E^{\ddagger}$: | 7.0 | 6.1 | 7.1 | 6.8 |
|  |  | $\Delta G^{\ddagger}$: | 21.8 | 21.1 | 22.7 | 19.7 |

Example 2—Preparation of Dibenzocyclooctynes

Scheme 1. Synthesis of 2-Azabenzo-8-chlorobenzocyclooctyne

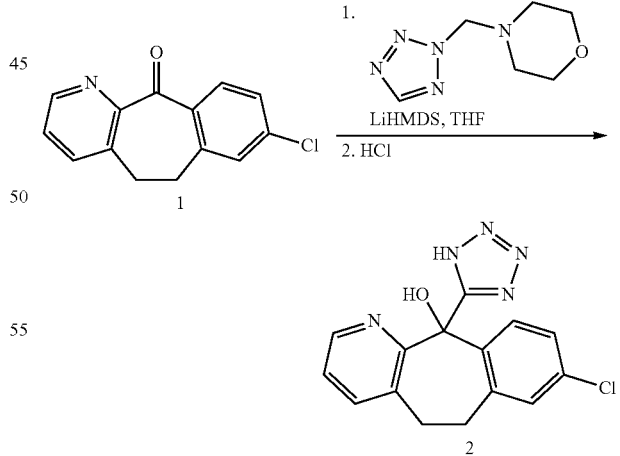

Synthesis of 4-((N-Tetrazolyl)methyl)morpholine.

To a cold (0° C.), stirred solution of tetrazole (0.70 g, 10.0 mmol, 1.0 equiv) in methanol (10 mL) was added morpholine (0.957 g, 0.95 mL, 11.0 mmol, 1.1 equiv), and the mixture was stirred for 15 min. An aqueous solution of 37% v/v formaldehyde (0.98 mL, 12.0 mmol, 1.2 equiv) was added dropwise, and the mixture was stirred overnight at room temperature. The reaction mixture was then concentrated under reduced pressure, and the residue was recrystallized from a 1:2 v/v mixture of $CH_2Cl_2$ and hexanes to give 4-((N-Tetrazolyl)methyl)morpholine as a mixture of N tautomers, as white crystals (1.48 g, 8.74 mmol, 88% yield).

$^{1}$H NMR (400 MHz, $CDCl_3$, δ): 8.67 (s, 0.2H), 8.56 (s, 0.8H), 5.53 (s, 1.6H), 5.31 (s, 0.4H), 3.82-3.61 (m, 4H), 2.69-2.65 (m, 3.2H), 2.62 (t, J=4.7 Hz, 0.8H). $^{13}$C NMR (101 MHz, $CDCl_3$, δ): 152.69, 74.00, 66.64, 66.44, 49.85, 49.76. HRMS m/z calcd for $C_6H_{12}N_5O$ [M+H]$^+$, 170.10364; found, 170.10408.

Synthesis of 8-Chloro-11-(1H-tetrazol-5-yl)-6,11-dihydro-5H-benzo[5,6]cyclohepta[1,2-b]pyridin-11-ol (2)

To a stirred solution of 4-((N-tetrazolyl)methyl)morpholine (0.70 g, 8.24 mmol, 2.0 equiv) and 8-chloro-5H-benzo[5,6]cyclohepta[1,2-b]pyridin-11(6H)-one (1; 0.5 g, 4.12 mmol, 1.0 equiv) in THF (10 mL), under $N_2$(g) at −78° C. (acetone/$CO_2$), was added 1 M LiHMDS in THF (4.33 mL, 4.33 mmol, 2.1 equiv) dropwise via a syringe. The reaction mixture was stirred for 2 h at −78° C. then allowed to warm to room temperature overnight. The reaction mixture was concentrated under reduced pressure, and the remaining residue was treated with aqueous HCl (1 M, 25 mL) and stirred at room temperature for 1 h. The solution was then extracted with EtOAc (3×50 mL), and the combined organic extracts were dried over Na₂SO₄(s), filtered, and concentrated under reduced pressure. The residue was purified by flash column chromatography on silica gel (hexanes/EtOAc 85:15→25:75) to provide compound 2 (672 mg, 2.14 mmol, 52% yield) as a white solid.

¹H NMR (500 MHz, chloroform-d, δ): 8.78 (s, 1H), 8.46 (s, 1 H), 8.09 (dd, J=8.4, 4.0 Hz, 1H), 7.64 (d, J=7.6 Hz, 1H), 7.37 (d, J=6.6 Hz, 1H), 7.25 (d, J=8.9 Hz, 1H), 7.17 (s, 1H), 3.40-3.32 (m, 1H), 3.05-2.93 (m, 3H), 2.74-2.67 (m, 1H). ¹³C NMR (126 MHz, chloroform-d, δ): 161.98, 152.43, 143.57, 142.67, 141.72, 140.09, 138.54, 134.70, 134.38, 129.45, 127.21, 126.36, 124.64, 30.81, 29.95. HRMS m/z calcd for C₁₅H₁₃ON₅Cl [M+H]⁺, 314.08086; found, 314.08960.

Synthesis of 2-Azabenzo-8-chlorobenzocyclooctyne (ABC-3).

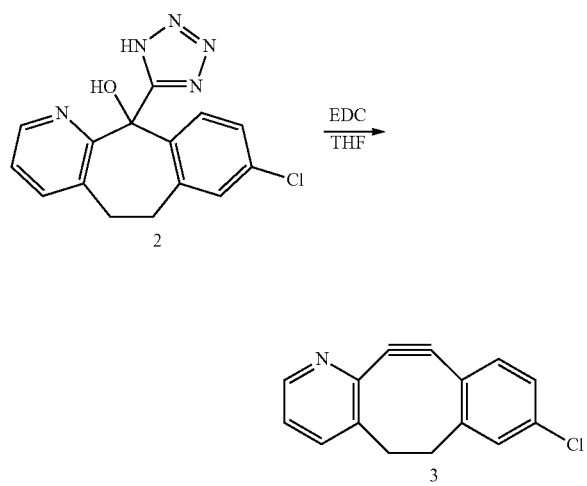

To a stirred solution of compound 2 (0.514 g, 1.64 mmol, 1.0 equiv) in THF (5.0 mL), was treated with EDC (0.345 mg, 1.80 μmol, 1.1 equiv) and allowed to react overnight. The reaction mixture was concentrated under reduced pressure, and the residue was purified by flash column chromatography on silica gel (hexanes/EtOAc 85:15→25:75) to provide compound 3 (157 mg, 0.66 mmol, 40% yield) as a pale yellow solid. mp: decomposition observed at ≥80° C.

¹H NMR (500 MHz, chloroform-d, δ): 8.44 (dd, J=5.0, 1.6 Hz, 1 H), 7.51 (dd, J=7.6, 1.6 Hz, 1H), 7.30-7.20 (m, 3H), 7.12 (dd, J=7.7, 4.9 Hz, 1H), 3.30-3.18 (m, 2H), 2.36 (ddq, J=15.1, 8.5, 3.7 Hz, 2H). ¹³C NMR (126 MHz, chloroform-d, δ): 155.00, 148.55, 147.75, 144.65, 136.34, 134.52, 129.74, 127.45, 126.88, 121.97, 121.20, 113.31, 109.88, 35.62, 34.79. HRMS m/z calcd for C₁₅H₁₁NCl [M+H]⁺, 240.05800; found, 240.06485.

Synthesis of 5-(1H-Tetrazol-5-yl)-10,11-dihydro-5H-dibenzo[a,d][7]annulen-5-ol (5).

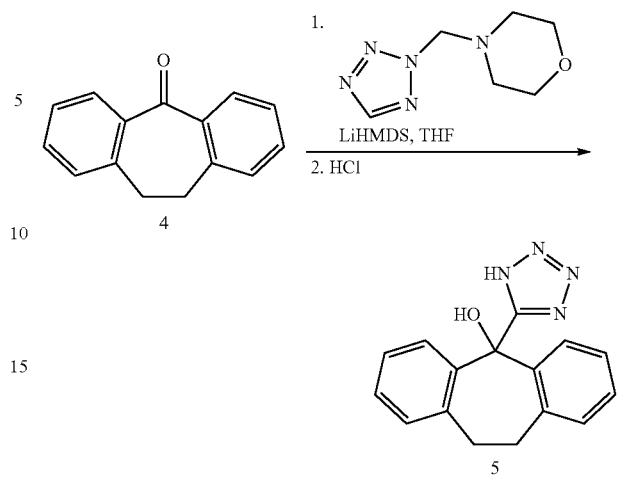

To a stirred solution of 4-((N-tetrazolyl)methyl)morpholine (0.70 g, 8.24 mmol, 2.0 equiv) and dibenzosuberone (4; 0.25 g, 1.22 mmol, 1.0 equiv) in THF (5 mL), under N₂(g) at −78° C. (acetone/CO₂), was added 1 M LiHMDS in THF (2.56 mmol, 2.56 mL, 2.1 equiv) dropwise via a syringe. The reaction mixture was stirred for 2 h at −78 ° C. then allowed to warm to room temperature overnight. The reaction mixture was concentrated under reduced pressure, and the remaining residue was treated with aqueous HCl (1 M, 25 mL) and stirred at room temperature for 1 h. The solution was then extracted with EtOAc (3×50 mL), and the combined organic extracts were dried over Na₂SO₄(s), filtered, and concentrated under reduced pressure. The residue was purified by flash column chromatography on silica gel (2% v/v MeOH in CH₂Cl₂) to provide compound 5 (0.3596 g) as a white solid with some impurities and was used in the next step without further purification.

¹H NMR (400 MHz, MeOD, δ): 8.09-7.99 (m, 2H), 7.31-7.25 (m, 4H), 7.18-7.12 (m, 2H), 2.83 (s, 4H). ¹³C NMR (101 MHz, MeOD, δ): 162.16, 141.12, 137.93, 130.25, 128.05, 125.83, 125.22, 71.82, 32.05. HRMS m/z calcd for C₁₆H₁₅ON₄ [M+H]⁺, 279.12458; found, 279.12665.

Synthesis of Dibenzocyclooctyne (DIBO-6).

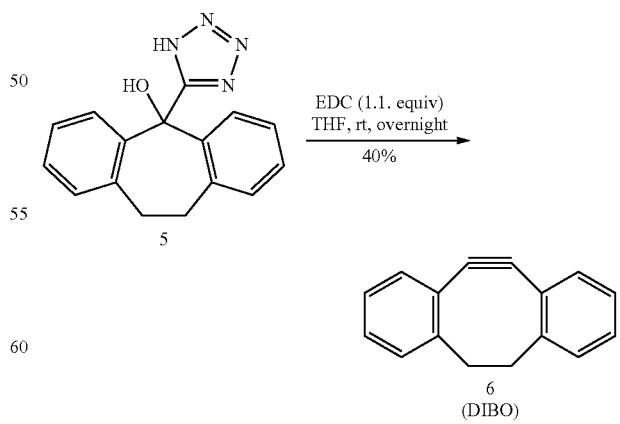

A stirred solution of compound 5 (0.200 g, 0.72 mmol, 1.0 equiv) in CH₂Cl₂ (4 mL) was treated with N,N'-diisopropylcarbodiimide (DIC) (0.109 g, 0.86 mmol, 1.2 equiv) and allowed to react overnight. The reaction mixture was concentrated under reduced pressure and purified by flash column chromatography on silica gel (hexanes) to provide DIBO (6; 0.072 g, 0.373 mmol, 55% yield for 3 steps from dibenzosuberone) as a white solid.

$^1$H NMR (500 MHz, CDCl$_3$, δ): 7.38-7.31 (m, 4H), 7.31-7.26 (m, 4aH), 3.38-3.29 (m, 2H), 2.50-2.40 (m, 2H). $^{13}$C NMR (126 MHz, CDCl$_3$, δ): 153.62, 129.41, 127.69, 126.52, 126.12, 123.95, 111.55, 36.47. HRMS m/z calcd for C$_{16}$H$_{13}$ [M+H]$^+$, 205.10172; found, 205.10245.

Example 3—1,3-Dipolar Cycloaddition Reactions

General Procedure A. Azides or diazo compounds were dissolved in anhydrous CH$_2$Cl$_2$ (0.5 mL) in a scintillation vial at room temperature with stirring. To this solution was added a solution of cyclooctyne in anhydrous CH$_2$Cl$_2$ (0.5 mL), and the reaction mixture was stirred overnight. The reaction mixture was concentrated under reduced pressure, and the residue was purified by flash column chromatography on silica gel (hexanes/EtOAc 85:15→25:75) to provide the desired product.

Synthesis of N-Methyl-N-benzyl-2-bromoacetamide (7).

To a stirred solution of N-methylbenzylamine (606 mg, 5 mmol, 1.0 equiv) and triethylamine (0.7 mL, 5 mmol, 1.0 equiv) in anhydrous CH$_2$Cl$_2$ (10 mL) was added a solution of bromoacetyl bromide (1.06 g, 5.25 mmol, 1.05 equiv) in CH$_2$Cl$_2$ (2 mL) dropwise at 0° C. The resulting mixture was allowed to react for 4 h at room temperature. The reaction was quenched with saturated NaHCO$_3$ (10 mL) at 0° C., extracted with diethyl ether (3×25 mL), washed with brine, dried over Na$_2$SO$_4$(s), filtered and concentrated under reduced pressure. The resultant crude material was used in subsequent steps without further purification.

Synthesis of 2-Azido-N-methyl-N-(phenylmethyl)acetamide (8).

To a stirred solution of ethyl diazoacetate (1.34 g, 5.53 mmol, 1 equiv) in DMF (25 mL), was added sodium azide (0.719 g, 11.06 mmol, 2.0 equiv) and the resulting mixture was allowed to react overnight at room temperature. A mixture of H$_2$O/Et$_2$O 1:1 was added to the reaction mixture, and the aqueous phase was extracted with Et$_2$O (3×25 mL), the organic extract was then washed with water (8×20 mL) and brine, and dried over Na$_2$SO$_4$(s). The resulting mixture was concentrated under reduced pressure, and the residue was purified by flash column chromatography on silica gel (hexanes/EtOAc 85:15→25:75) to provide compound 8 (0.351 g, 31% yield) as a colorless oil.

$^1$H NMR (500 MHz, chloroform-d, δ): 7.31 (ddd, J=34.5, 19.6, 7.7 Hz, 5H), 7.15 (d, J=7.5 Hz, 1H), 4.61 (s, 1H), 4.45 (s, 1 H), 3.96 (d, J=11.2 Hz, 2H), 3.01 (s, 1H), 2.86 (s, 2H). $^{13}$C NMR (126 MHz, chloroform-d, δ): 167.29, 136.47, 135.57, 129.15, 128.73, 128.24, 128.00, 127.70, 126.21, 52.76, 51.25, 50.64, 50.51, 34.38, 33.88. HRMS m/z calcd for C$_{10}$H$_{13}$ON$_4$ [M+H]$^+$, 205.10894; found, 205.11737.

Synthesis of 2-Diazo-N-methyl-N-(phenyl methyl)acetamide (9).

Compound 8 (0.120 g, 0.586 mmol, 1.0 equiv) was dissolved in H$_2$O/THF 1:9 (20 mL). To this solution was added 2,5-dioxopyrrolidin-1-yl 3-(diphenylphosphanyl)propanoate (0.219 g, 0.615 mmol, 1.05 equiv), and the reaction mixture was stirred for 4 h at room temperature before a saturated aqueous solution of NaHCO$_3$ (15 mL) was added. The reaction mixture was then stirred vigorously for 3 h. The reaction mixture was diluted with brine and extracted with CH$_2$Cl$_2$ (3×). The combined organic extracts were dried over Na$_2$SO$_4$(s), filtered, and concentrated under reduced pressure, and the residue was purified with silica gel chromatography (hexanes/EtOAc 50:50) to give compound 9 (33.3 mg, 29% yield).

$^1$H NMR (400 MHz, chloroform-d, δ): 7.40-7.21 (m, 5H), 5.01 (s, 1 H), 4.65-4.38 (m, 2H), 2.89 (s, 3H). $^{13}$C NMR (101 MHz, chloroform-d, δ): 166.14, 128.78, 127.55, 46.53, 34.33, 33.98, 25.64, 24.97. HRMS m/z calcd for C$_{10}$H$_{12}$ON$_3$ [M+H]$^+$, 190.09804; found, 190.10475.

Synthesis of 2-(11-chloro-8,9-dihydro-3H-benzo[5,6][1,2,3]triazolo[4',5':7,8]cycloocta[1,2-b]pyridin-3-yl)-N-methylacetamide (10).

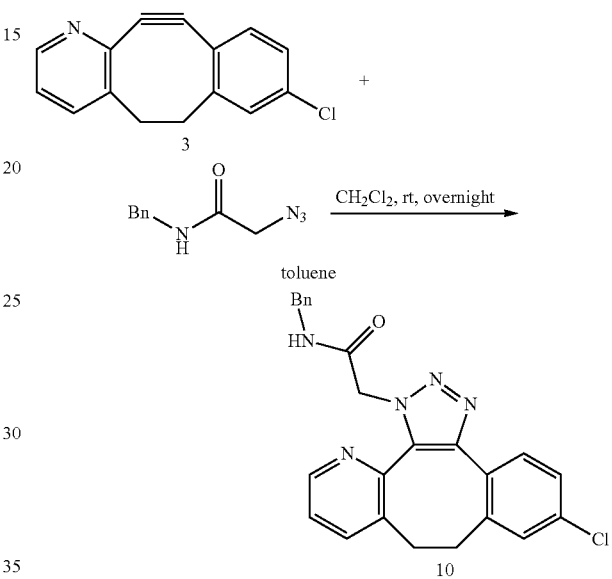

Following Cycloaddition General Procedure A, a solution of N-benzylazidoacetamide (7.989 mg, 0.042 mmol) dissolved in anhydrous CH$_2$Cl$_2$ was treated with compound 3 (10 mg, 0.042 mmol) to provide compound 10.

$^1$H NMR (500 MHz, chloroform-d, δ): 8.27 (dd, J=4.7, 1.6 Hz, 1 H), 7.65 (dd, J=7.9, 1.6 Hz, 1H), 7.53 (d, J=8.2 Hz, 1H), 7.49 (t, J=5.9 Hz, 1H), 7.35-7.18 (m, 8H), 5.26 (s, 2H), 4.47 (d, J=5.7 Hz, 2H), 3.22 (dd, J=8.3, 5.0 Hz, 2H), 3.13 (dd, J=8.3, 5.0 Hz, 2H). $^{13}$C NMR (126 MHz, chloroform-d, δ): 171.19, 165.82, 147.31, 144.97, 144.36, 140.34, 139.83, 137.80, 136.56, 134.59, 134.46, 132.25, 129.71, 128.70, 128.36, 127.68, 127.56, 126.93, 123.85, 52.64, 43.62, 34.24, 33.31. HRMS m/z calcd for C$_{24}$H$_{21}$ON$_5$Cl [M+H]$^+$, 430.14346; found, 430.16281.

Synthesis of N-benzyl-11-chloro-8,9-dihydro-1H-benzo[5,6]pyrazolo[3',4':7,8]cycloocta[1,2-b]pyridine-3-carboxamide (11).

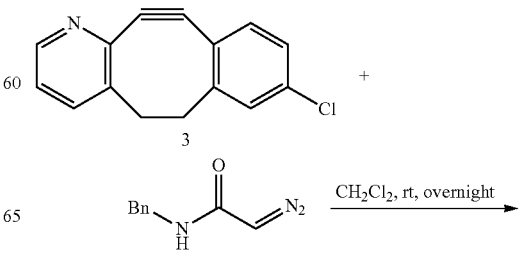

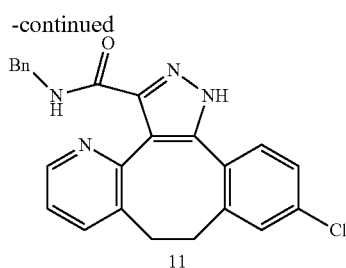

Following Cycloaddition General Procedure A, a solution of N-benzyldiazidoacetamide (7.358 mg, 0.042 mmol) dissolved in anhydrous CH$_2$Cl$_2$ was treated with compound 3 (10 mg, 0.042 mmol) to provide compound 11.

$^1$H NMR (500 MHz, chloroform-d, δ): 9.77 (s, 1H), 8.10 (dd, J=4.8, 1.7 Hz, 1H), 7.66 (dd, J=7.8, 1.7 Hz, 1H), 7.37-7.12 (m, 3H), 7.25 (m, 3H), 7.19 (d, J=2.2 Hz, 1H), 7.15 (m, 2H), 4.58 (d, J=5.2 Hz, 2H), 3.34-3.22 (m, 2H), 3.11 (d, J=7.1 Hz, 2H). $^{13}$C NMR (126 MHz, chloroform-d, δ): 159.67, 146.36, 139.54, 138.91, 137.34, 136.84, 134.22, 134.01, 130.07, 128.67, 127.81, 127.51, 126.46, 123.01, 43.92, 35.45, 32.34. HRMS m/z calcd for C$_{24}$H$_{20}$ON$_4$Cl [M+H]$^+$, 415.13256; found, 415.14917.

Synthesis of N-benzyl-2-(11-chloro-8,9-dihydro-3H-benzo[5,6][1,2,3]triazolo[4',5':7,8]cycloocta[1,2-b]pyridin-3-yl)-N-methylacetamide (12).

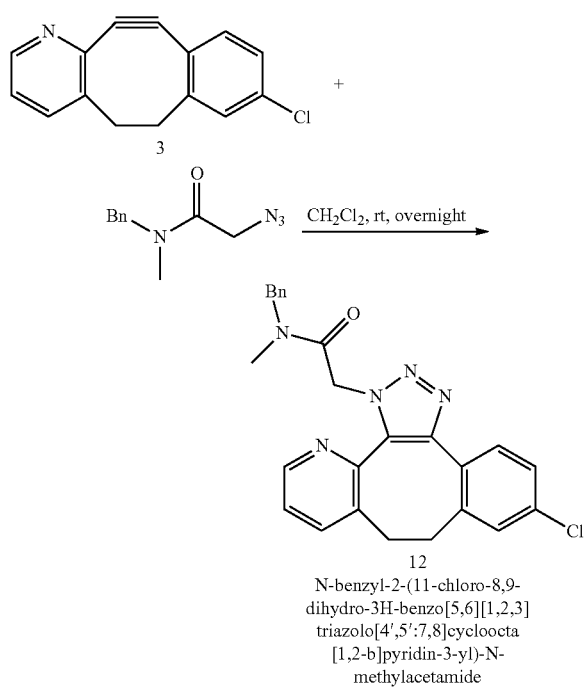

12
N-benzyl-2-(11-chloro-8,9-dihydro-3H-benzo[5,6][1,2,3]triazolo[4',5':7,8]cycloocta[1,2-b]pyridin-3-yl)-N-methylacetamide Following Cycloaddition General Procedure A, a solution of compound 11 (8.578 mg, 0.042 mmol) dissolved in anhydrous CH$_2$Cl$_2$ was treated with compound 3 (10 mg, 0.042 mmol) to provide compound 12 as regioisomers.

$^1$H NMR (500 MHz, chloroform-d, δ): 8.45 (dd, J=4.7, 1.7 Hz, 1 H), 8.37 (dd, J=4.8, 1.6 Hz, 0.5H), 7.66 (ddd, J=7.5, 5.6, 1.7 Hz, 2H), 7.55 (d, J=8.3 Hz, 2H), 7.53 (d, J=8.3 Hz, 1H), 7.41-7.33 (m, 2H), 7.25 (m, 8H), 7.13-7.07 (m, 1H), 6.94-6.86 (m, 2H), 5.73 (s, 3H), 4.58 (s, 1H), 4.46 (s, 2H), 3.35-3.30 (m, 3H), 3.27 (dd, J=8.1, 4.7 Hz, 3H), 2.96 (s, 3H), 2.87 (s, 2H). $^{13}$C NMR (126 MHz, chloroform-d, δ): 165.51, 165.25, 147.08, 146.98, 146.16, 146.03, 144.96, 144.93, 140.61, 139.37, 139.32, 136.84, 136.73, 136.29, 135.41, 134.77, 134.62, 134.16, 134.14, 132.42, 129.81, 129.78, 129.18, 128.88, 128.86, 128.62, 128.04, 127.75, 127.54, 126.68, 126.67, 126.29, 123.37, 123.31, 52.70, 51.28, 50.32, 50.11, 34.49, 34.02, 33.98, 33.88. HRMS m/z calcd for C$_{25}$H$_{23}$ON$_5$Cl [M+H]$^+$, 444.15911; found, 444.18030.

Synthesis of N-benzyl-11-chloro-N-methyl-8,9-dihydro-1H-benzo[5,6]pyrazolo[3',4':7,8]cycloocta[1,2-b]pyridine-3-carboxamide (13).

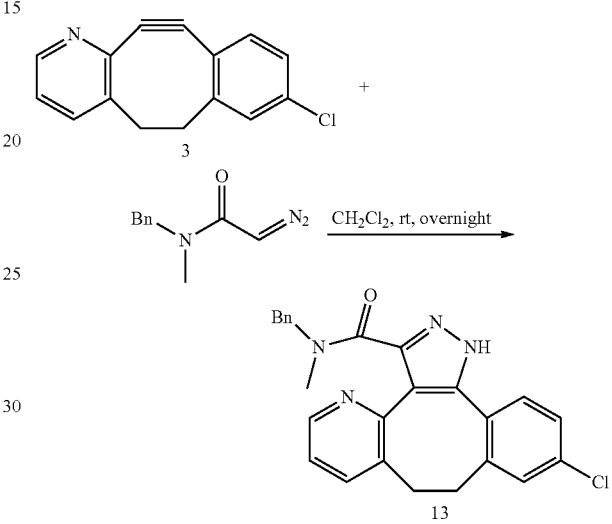

Following Cycloaddition General Procedure A, a solution of compound 12 (8.136 mg, 0.042 mmol) dissolved in anhydrous CH$_2$Cl$_2$ was treated with compound 3 (10 mg, 0.042 mmol) to provide compound 13 as regioisomers.

$^1$H NMR (500 MHz, chloroform-d, δ): 8.43 (d, J=4.7 Hz, 1H), 8.34-8.27 (m, 0.59H), 7.51 (d, J=7.5 Hz, 2H), 7.35-7.20 (m, 12H), 7.16-7.03 (m, 3H), 4.69 (s, 3H), 3.25-3.19 (m, 2H), 3.19-3.09 (m, 5H), 2.89 (s, 2H), 2.87 (s, 3H). $^{13}$C NMR (126 MHz, chloroform-d, δ): 164.85, 164.36, 149.68, 149.43, 146.90, 143.64, 143.39, 141.45, 139.26, 136.76, 136.51, 134.97, 134.83, 133.86, 131.49, 129.94, 129.81, 128.56, 128.49, 128.23, 128.14, 127.59, 127.39, 127.32, 126.76, 122.05, 121.92, 121.07, 54.84, 50.94, 36.07, 34.66, 34.45, 33.61, 33.53, 32.82. HRMS m/z calcd for C$_{25}$H$_{22}$ON$_4$Cl [M+H]$^+$, 429.14821; found, 429.16635.

Synthesis of ethyl 11-chloro-8,9-dihydro-1H-benzo[5,6]pyrazolo[3',4':7,8]cycloocta[1,2-b]pyridine-3-carboxylate (14).

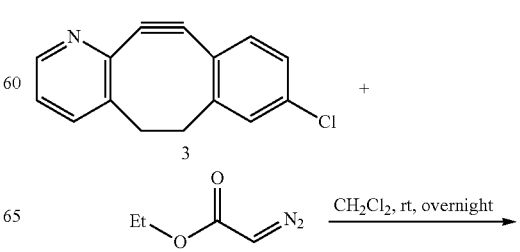

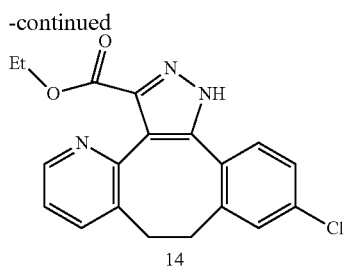

Following Cycloaddition General Procedure A, a solution of ethyl diazoacetate (4.792 mg, 0.042 mmol) dissolved in anhydrous $CH_2Cl_2$ was treated with compound 3 (10 mg, 0.042 mmol) to provide compound 14.

$^1$H NMR (500 MHz, chloroform-d, δ): 8.46 (dd, J=4.7, 1.7 Hz, 1 H), 7.56 (d, J=7.8 Hz, 1H), 7.26 (d, J=8.3 Hz, 1H), 7.20 (d, J =2.2 Hz, 1H), 7.17-7.12 (m, 2H), 4.27 (q, J=7.1 Hz, 2H), 3.14 (q, J=4.0 Hz, 4H), 1.19 (t, J=7.1 Hz, 3H). $^{13}$C NMR (126 MHz, chloroform-d, δ): 159.93, 147.02, 140.57, 137.99, 134.84, 134.63, 132.06, 130.18, 129.21, 126.63, 122.63, 61.27, 34.65, 33.07, 13.95. HRMS m/z calcd for $C_{19}H_{17}O_2N_3Cl$ [M+H]$^+$, 354.10093; found, 354.11700.

Synthesis of 2-(8,9-dihydro-1H-dibenzo[3,4:7,8]cycloocta [1,2-d][1,2,3]triazol-1-yl)-N-methylacetamide (15).

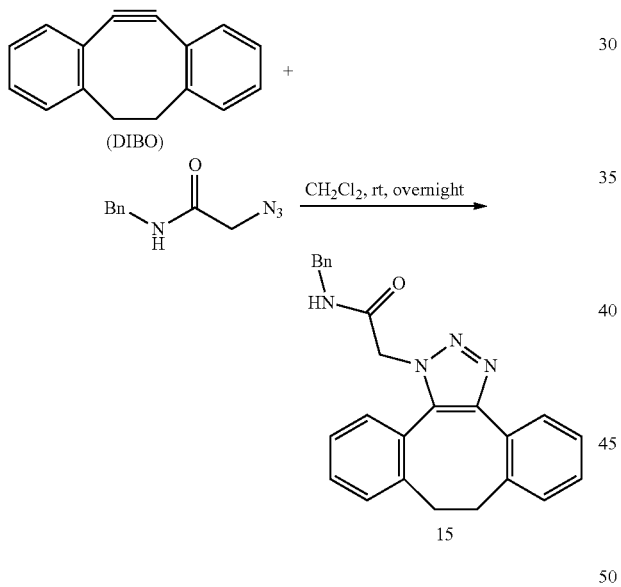

Following Cycloaddition General Procedure A, a solution of N-benzylazidoacetamide (7.989 mg, 0.042 mmol) dissolved in anhydrous $CH_2Cl_2$ was treated with DIBO (10 mg, 0.042 mmol) to provide compound 15.

$^1$H NMR (500 MHz, chloroform-d, δ): 7.55-7.48 (m, 1H), 7.41-7.17 (m, 12H), 7.14 (dd, J=7.4, 1.2 Hz, 1H), 5.16 (d, J=16.4 Hz, 1H), 5.03 (d, J=16.6 Hz, 1H), 4.53 (dd, J=14.7, 6.0 Hz, 1H), 4.43 (dd, J=14.9, 5.4 Hz, 1H), 3.35 (td, J=12.1, 10.3, 4.5 Hz, 1H), 3.15-3.03 (m, 2H), 2.92-2.81 (m, 1H). $^{13}$C NMR (126 MHz, chloroform-d, δ): 165.43, 147.01, 141.71, 137.85, 137.27, 135.18, 131.70, 130.92, 130.46, 130.25, 129.23, 129.01, 128.81, 128.41, 127.77, 127.72, 126.80, 126.13, 125.14, 51.32, 43.75, 36.34, 33.02. HRMS m/z calcd for $C_{25}H_{23}N_4O$ [M+H]$^+$, 395.18718; found, 395.19003.

Synthesis of N-benzyl-8,9-dihydro-1H-dibenzo[3,4:7,8]cycloocta[1,2-c]pyrazole-3-carboxamide (16).

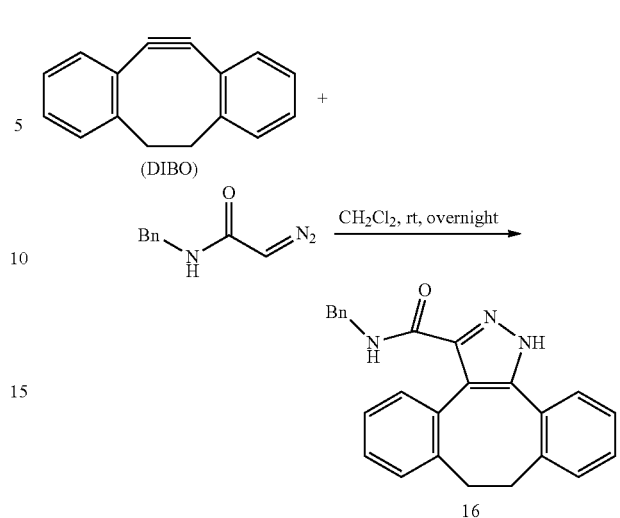

Following Cycloaddition General Procedure A, a solution of N-benzyldiazidoacetamide (7.350 mg, 0.042 mmol) dissolved in anhydrous $CH_2Cl_2$ was treated with DIBO (10 mg, 0.042 mmol) to provide compound 16.

$^1$H NMR (500 MHz, chloroform-d, δ): 11.58 (s, 1H), 7.34-7.08 (m, 13H), 6.84 (s, 1H), 4.73-4.57 (m, 1H), 4.50-4.39 (m, 1H), 3.44-2.87 (m, 4H). $^{13}$C NMR (126 MHz, chloroform-d, δ): 171.21, 160.59, 140.56, 139.01, 137.82, 131.05, 130.95, 130.91, 130.88, 129.85, 128.68, 128.64, 128.30, 127.69, 127.45, 126.09, 126.07, 120.39, 43.26, 36.30, 33.18. HRMS m/z calcd for $C_{25}H_{22}ON_3$ [M+H]$^+$, 380.17629; found, 380.185730.

Synthesis of ethyl 8,9-dihydro-1H-dibenzo[3,4:7,8]cycloocta[1,2-c]pyrazole-3-carboxylate (17).

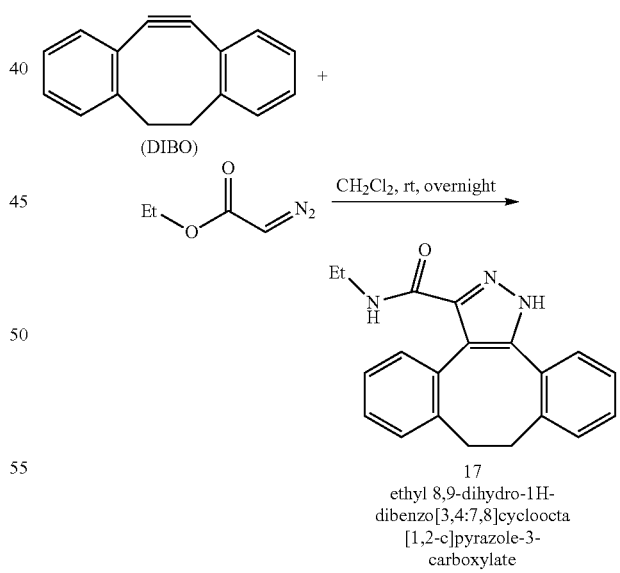

17
ethyl 8,9-dihydro-1H-
dibenzo[3,4:7,8]cycloocta
[1,2-c]pyrazole-3-
carboxylate Following Cycloaddition General Procedure A, a solution of compound ethyl diazoacetate (4.792 mg, 0.042 mmol) dissolved in anhydrous $CH_2Cl_2$ was treated with DIBO (10 mg, 0.042 mmol) to provide compound 17.

$^1$H NMR (500 MHz, chloroform-d, δ): 7.70-7.35 (m, 1H), 7.35 (s, 0H), 7.34-7.08 (m, 8H), 4.33 (d, J=49.5 Hz, 2H), 3.48-2.81 (m, 4H), 1.28 (t, J=7.7 Hz, 3H). $^{13}$C NMR (126

MHz, chloroform-d, δ): 160.55, 139.83, 139.11, 131.55, 131.12, 131.06, 130.76, 129.69, 129.07, 128.83, 128.02, 126.06, 125.33, 123.61, 61.20, 36.44, 32.95, 31.60, 14.21, 14.13, 14.09. HRMS m/z calcd for $C_{20}H_{19}N_2O_2$ $[M+H]^+$, 319.14465; found, 319.14713.

Example 4—Kinetic Analyses

The rates of reaction for the 1,3-dipolar cycloaddition of dipoles N-benzylazidoacetamide and N-benzyldiazoacetamide with compound 3 in both aprotic ($CH_2Cl_2$) and protic solvents (MeOH and PBS containing 2% v/v DMSO) were measured. The depletion of compound 3 by using HPLC and second-order rate constants were calculated from the slope of a plot of $[compound\ 3]^{-1}$ versus time. As a benchmark, the rate of the reaction of DIBO with each dipole was also measured.

The reaction rates with compound 3 were exceptionally high (FIG. 1). In all solvent conditions, each acetamide dipole displayed rate constants with compound 3 that exceed those attainable with commercially available cyclooctyne reagents. In $CH_2Cl_2$, the rate constants are among the highest reported for both SPAAC and the analogous diazoacetamide reaction. The strategic CH→N substitution that converts DIBO to compound 3, leads to 1,200 and 30-fold rate increases with N-benzyl diazoacetamide and N-benzylazidoacetamide, respectively.

A significantly larger rate constant for N-benzyldiazoacetamide over the N-benzylazidoacetamide provides experimental corroboration of the prediction of a more optimal geometry for its hydrogen bond (vide supra). With DIBO, the N-azidoacetamide reacts 2- to 3-fold faster than does the N-diazoacetamide, in agreement with the reactions of DIBAC and 4-Dibenzocyclooctynone (DIBONE). The ~20-fold rate increase of N-benzyl diazoacetamide over N-benzyl azidoacetamide with compound 3 exceeds that of both the biaryl systems as well as sulfur, nitrogen, and oxygen-containing heterocyclic cyclooctynes (SNO-OCTs).

To assess the effect of the putative hydrogen bond, the reactivity of compound 3 and DIBO with ethyl diazoacetate, which lacks a hydrogen bond donor, was tested. The rate constant for the reaction of compound 3 with ethyl diazoacetate was nearly 200-fold lower than that with N-benzylazidoacetamide. This decrease is substantially greater than the 4-fold decrease in rate constant for the reaction of these same dipoles with DIBO (FIG. 1).

The existence of the hydrogen bond was corroborated by comparing the regiochemistry of cycloadducts. To do so, $^1$H-NMR spectra of the products of the cycloadditions of N-benzylazidoacetamide and N-benzyldiazoacetamide with compound 3 were compared to the $^1$H-NMR of the cycloaddition products of N-methylated derivatives of N-benzylazidoacetamide and N-benzyldiazoacetamide with compound 3. Methylation of the amide in N-benzylazidoacetamide and N-benzyldiazoacetamide impedes the formation of hydrogen bonds, allowing for direct comparison of its importance through their regioselectivity. $^1$H-NMR studies revealed that regioselectivity is attained only when a hydrogen bond is made in the transition state (FIG. 2A, FIG. 2B).

Figure 2:
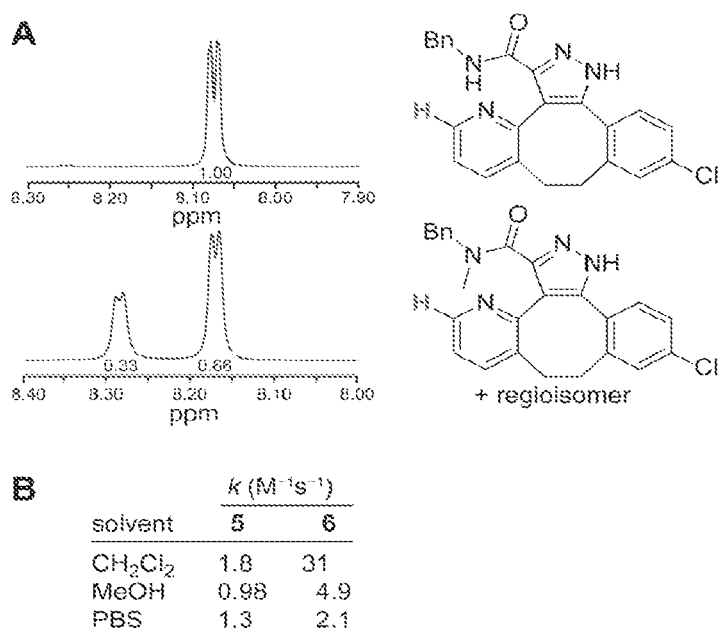
FIG. 2 shows the effect of hydrogen bonding on the 1,3-dipolar cycloaddition of compound 3 with N-benzyldiazoacetamide. (A) $^1H$ NMR shifts of the C3-H (red) proton in the product of the cycloaddition of compound 3 with N-benzyldiazoacetamide, or its N-methyl derivative in $CH_2Cl_2$. (B). Second-order rate constants for the reaction of ABC with dipoles N-benzylazidoacetamide and N-benzyldiazoacetamide in $CH_2Cl_2$ (as in FIG. 1), MeOH, and PBS containing DMSO (2% v/v). Values are the mean from triplicate experiments.

The use of protic solvents diminishes the effect of the hydrogen bonds and lowers the observed rates (FIG. 2B). Interestingly, the azidoacetamides display much smaller differences in reactivity. Again, this observation is consistent with a weaker hydrogen bond. Nevertheless, the reaction rates observed in protic solvents are among the highest reported for a SPAAC.

Kinetics General Method A. Stock solutions at the specified concentrations in the specified solvents were prepared for each dipole and dipolarophile. Aliquots (0.5 mL) of dipole and dipolarophile were mixed, and reactions were monitored by HPLC with aliquots injected at the timepoints shown in the kinetic traces below. Each reaction was carried out in triplicate. The concentration of remaining dipolarophile was obtained from its corresponding peak in the chromatogram monitored at 280 nm. Second-order rate constants were calculated from the slope of the plot of $[dipolarophile]^{-1}$ versus time.

Figure 3:
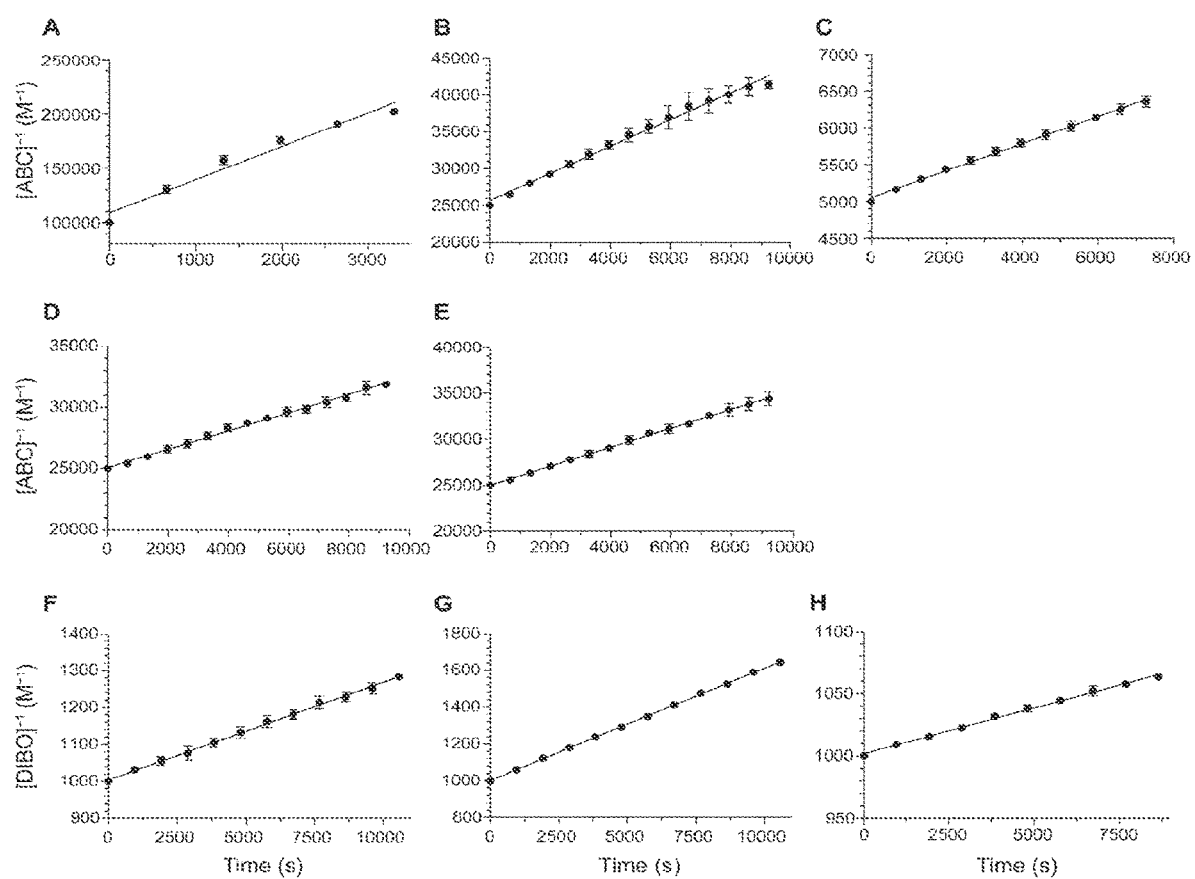
FIG. 3 shows kinetic traces for the reactions of compound 3 with (A) N-benzylazidoacetamide, (B) N-benzyldiazoacetamide, compound, (C) ethyl diazoacetate, (D) 2-Azido-N-methyl-N-(phenylmethyl)acetamide (k=1.0 $M^{-1}s^{-1}$), and (E) 2-Diazo-N-methyl-N-(phenylmethyl)acetamide (k=0.75 $M^{-1}s^{-1}$), and the reactions of DIBO with (F) N-benzylazidoacetamide, (G) N-benzyldiazoacetamide, and (H) ethyl diazoacetate. All reactions were carried out in $CH_2Cl_2$ at 26° C. and were monitored by HPLC. Values are the mean±SD for triplicate experiments.
Figure 4:
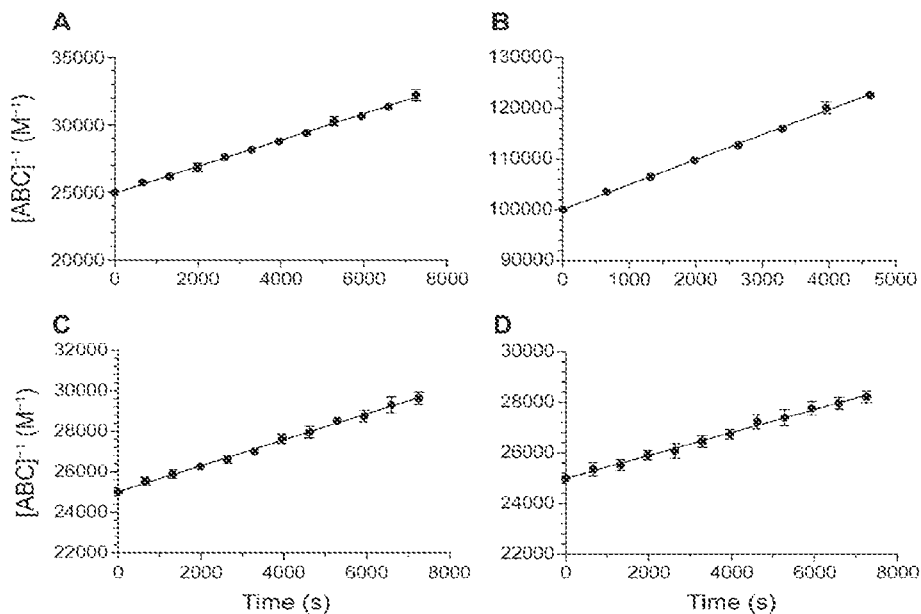
FIG. 4 shows kinetic traces for the reactions of compound 3 with (A) N-benzylazidoacetamide, (B) N-benzyldiazoacetamide, compound, (C) ethyl diazoacetate, (D) 2-Azido-N-methyl-N-(phenylmethyl)acetamide. All reactions were carried out in MeOH at 26° C. and were monitored by HPLC. Values are the mean±SD for triplicate experiments.
Figure 5:
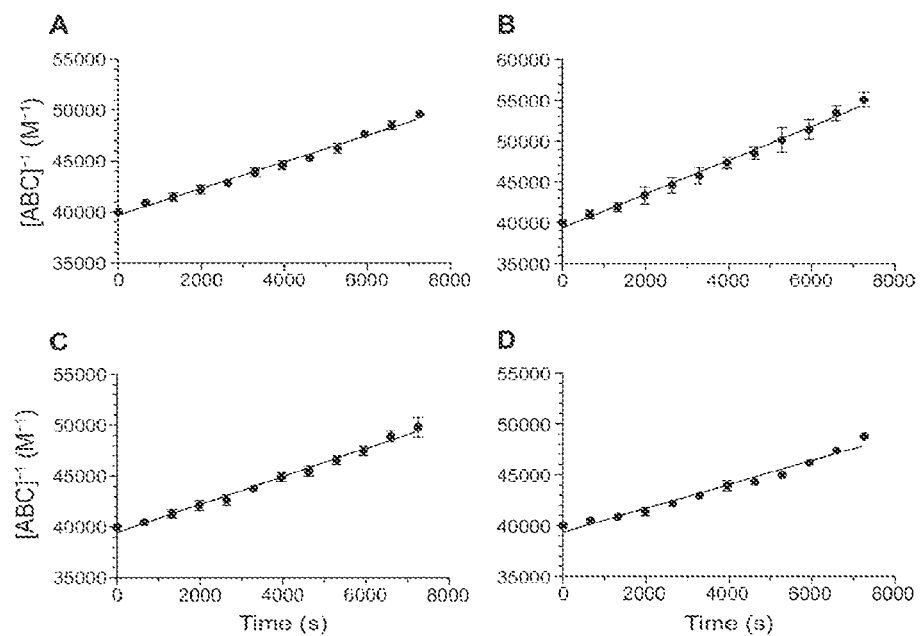
FIG. 5 shows kinetic traces for the reactions of compound 3 with (A) N-benzylazidoacetamide, (B) N-benzyldiazoacetamide, compound, (C) ethyl diazoacetate, (D) 2-Azido-N-methyl-N-(phenylmethyl)acetamide. All reactions were carried out in PBS containing DMSO (2% v/v) at 26° C. and were monitored by HPLC. Values are the mean±SD for triplicate experiments.

Kinetics General Method B. Stock solutions of the specified dipoles and dipolarophiles were prepared in DMSO at 2.5 mM. An aliquot (10 µL) of each stock was added to 1 mL of PBS (final concentration: 25 µM), and reactions were monitored by HPLC with aliquots injected at the timepoints specified in FIG. 3. Each reaction was carried out in triplicate. The concentration of remaining dipolarophile was obtained from its corresponding peak in the chromatogram monitored at 280 nm. Second-order rate constants were calculated from the slope of the plot of $[dipolarophile]^{-1}$ versus time.

Reaction of N-benzylazidoacetamide with DIBO in $CH_2Cl_2$. Kinetics General Method A was followed using stock solutions at 2 mM and resulting in final reaction concentrations of 1 mM N-benzylazidoacetamide and 1 mM DIBO.

Reaction of N-benzyldiazoacetamide with DIBO in $CH_2Cl_2$. Kinetics General Method A was followed using stock solutions at 2 mM and resulting in final reaction concentrations of 1 mM N-benzyldiazoacetamide and 1 mM DIBO.

Reaction of N-benzylazidoacetamide with compound 3 in $CH_2Cl_2$. Kinetics General Method A was followed using stock solutions at 20 µM and resulting in final reaction concentrations of 10 µM N-benzylazidoacetamide and 10 µM compound 3.

Reaction of N-benzyldiazoacetamide with compound 3 in $CH_2Cl_2$. Kinetics General Method A was followed using stock solutions at 80 µM and resulting in final reaction concentrations of 40 µM N-benzyldiazoacetamide and 40 µM compound 3.

Reaction of ethyl diazoacetate with compound 3 in $CH_2Cl_2$. Kinetics General Method A was followed using stock solutions at 400 µM and resulting in final reaction concentrations of 200 µM ethyl diazoacetate and 200 µM compound 3.

Reaction of 2-Azido-N-methyl-N-(phenylmethyl)acetamide with compound 3 in $CH_2Cl_2$. Kinetics General Method A was followed using stock solutions at 80 µM and resulting in final reaction concentrations of 40 µM 2-Azido-N-methyl-N-(phenylmethyl)acetamide and 40 µM compound 3.

Reaction of compound 9 with compound 3 in $CH_2Cl_2$. Kinetics General Method A was followed using stock solutions at 80 µM and resulting in final reaction concentrations of 40 µM 2-Diazo-N-methyl-N-(phenylmethyl)acetamide and 40 µM compound 3.

Reaction of N-benzylazidoacetamide with compound 3 in MeOH. Kinetics General Method A was followed using stock solutions at 20 µM and resulting in final reaction concentrations of 10 µM N-benzylazidoacetamide and 10 µM compound 3.

Reaction of N-benzyldiazoacetamide with compound 3 in MeOH. Kinetics General Method A was followed using stock solutions at 80 µM and resulting in final reaction concentrations of 40 µM N-benzyldiazoacetamide and 40 µM compound 3.

Reaction of compound 8 with compound 3 in MeOH. Kinetics General Method A was followed using stock solutions at 80 µM and resulting in final reaction concentrations of 40 µM compound 8 and 40 µM compound 3.

Reaction of compound 9 with compound 3 in MeOH. Kinetics General Method A was followed using stock solutions at 80 µM and resulting in final reaction concentrations of 40 µM 2-Diazo-N-methyl-N-(phenylmethyl)acetamide and 40 µM compound 3.

Reaction of N-benzylazidoacetamide with compound 3 in PBS Containing DMSO (2% v/v). Kinetics General Method B was followed.

Reaction of N-benzyldiazoacetamide with compound 3 in PBS Containing DMSO (2% v/v). Kinetics General Method B was followed.

Reaction of compound 8 with compound 3 in PBS Containing DMSO (2% v/v). Kinetics General Method B was followed.

Reaction of compound 9 with compound 3 in PBS Containing DMSO (2% v/v). Kinetics General Method B was followed.

Example 5—Cyclooctyne Stability Experiments

The stability of ABC in the presence of biological nucleophiles was determined using a biomimetic concentration of glutathione, which contains amino, carboxyl, and sulfhydryl groups. DIBAC was used as a comparator.

Figure 6:
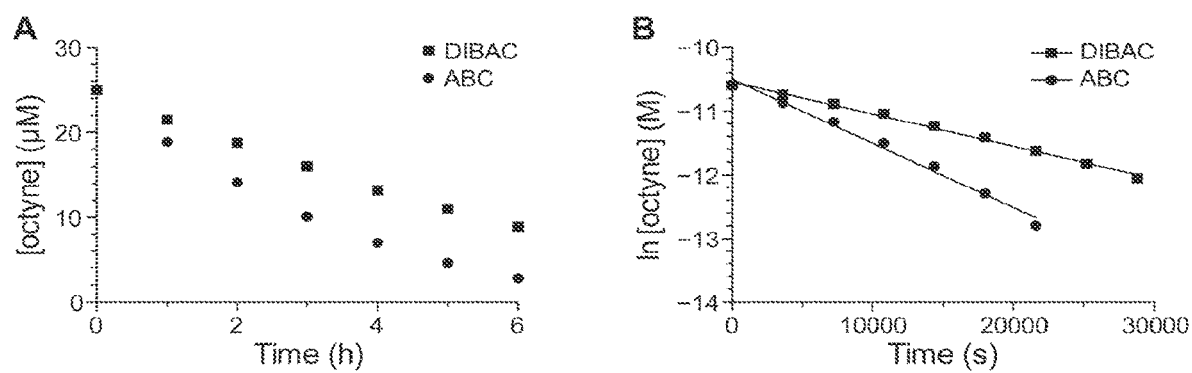
FIG. 6 shows the stability of DIBAC and compound 3 in the presence of 1 mM reduced glutathione and 0.2 mM oxidized glutathione in PBS containing DMSO (2% v/v) at 37° C. (A) Concentration of remaining DIBAC and compound 3 as determined by HPLC. (B) Natural logarithm of the concentration of DIBAC and compound 3 over time in order to determine second order rate constants of degradation. With respect to reduced glutathione, the second-order rate constants were 0.05 $M^{-1}s^{-1}$ and 0.10 $M^{-1}s^{-1}$ for DIBAC and compound 3, respectively. Values are the mean±SD for triplicate experiments. (Error bars are smaller than the data points.)

A solution of compound 3 (25 µM) or DIBAC (25 µM) was prepared in phosphate-buffered saline containing reduced glutathione (1.0 mM), oxidized glutathione (0.2 mM), and DMSO (2% v/v). The solutions were incubated at 37° C. (FIG. 6), and HPLC analyses were carried out every hour to determine the remaining concentration of dipolarophile. Subsequently, plots of In(concentration) versus time were prepared to calculate values of $k_{obs}$ for the degradation. These values were divided by the concentration of reduced glutathione to obtain second-order rate constants for the degradation with respect to reduced glutathione. The rates of degradation under these conditions were comparable, with second-order rate constants of 0.10 and 0.05 $M^{-1}s^{-1}$, respectively, for reaction with reduced glutathione.

The disclosed subject matter is not to be limited in scope by the specific embodiments and examples described herein. Indeed, various modifications of the disclosure in addition to those described will become apparent to those skilled in the art from the foregoing description and accompanying figures. Such modifications are intended to fall within the scope of the appended claims.

CITATIONS (1) Kolb, H. C.; Finn, M. G.; Sharpless, K. B. Click Chemistry: Diverse Chemical Function from a Few Good Reactions. *Angew. Chem., Int. Ed.* 2001, 40, 2004-2021.

(2) Huisgen, R. 1,3-Dipolar cycloadditions. Past and future. *Angew. Chem., Int. Ed.* 1963, 41, 2596-2599.

(3) Blomquist, A. T.; Liu, L. H. Many-Membered Carbon Rings. VII. Cycloöctyne. *J. Am. Chem. Soc.* 1953, 75, 2153-2154.

(4) Wittig, G.; Krebs, A. Zur Existenz niedergliedriger Cycloalkine, I. *Chem. Ber.* 1961, 94, 3260-3275.

(5) Banert, K.; Köhler, F. Synthesis of 1,4-Diazidobuta-1,3-dienes by Electrocyclic Ring Opening: Precursors for bi-2H-Azirin-2-yls and their Valence Isomerization to Diazabenzene. *Angew. Chem., Int. Ed.* 2001, 40, 174-177.

(6) Agard, N. J.; Prescher, J. A.; Bertozzi, C. R. A Strain-Promoted [3+2] Azide-Alkyne Cycloaddition for Covalent Modification of Biomolecules in Living Systems. *J. Am. Chem. Soc.* 2004, 126, 15046-15047.

(7) Agard, N. J.; Baskin, J. M.; Prescher, J. A.; Lo, A.; Bertozzi, C. R. A Comparative Study of Bioorthogonal Reactions with Azides. *ACS Chem. Biol.* 2006, 1, 644-648.

(8) Azido groups can survive cellular metabolic pathways (Saxon, E.; Bertozzi, C. R. Cell Surface Engineering by a Modified Staudinger Reaction. *Science* 2000, 287, 2007-2010). That is also true for diazo groups, which can likewise engage in 1,3-dipolar cycloadditions (Andersen, K. A.; Aronoff, M. R.; McGrath, N. A.; Raines, R. T. Diazo Groups Endure Metabolism and Enable Chemoselectivity in Cellulo. *J. Am. Chem. Soc.* 2015, 137, 2412-2415).

(9) Doering, W. v. E.; Roth, W. R. The Overlap of Two Allyl Radicals or a Four-Centered Transition State in the Cope Rearrangement. *Tetrahedron* 1962, 18, 67-74.

(10) Hill, R. K.; Rabinovitz, M. Stereochemistry of "No-Mechanism" Reactions: Transfer of Asymmetry in the Reaction of Olefins with Dienophiles. *J. Am. Chem. Soc.* 1964, 86, 965-966.

(11) Sletten, E. M.; Bertozzi, C. R. Bioorthogonal Chemistry: Fishing for Selectivity in a Sea of Functionality. *Angew. Chem., Int. Ed.* 2009, 48, 6974-6998.

(12) Patterson, D. M.; Nazarova, L. A.; Prescher, J. A. Finding the Right (Bioorthogonal) Chemistry. *ACS Chem. Biol.* 2014, 9, 592-605.

(13) Ess, D. H.; Houk, K. N. Distortion/Interaction Energy Control of 1,3-Dipolar Cycloaddition Reactivity. *J. Am. Chem. Soc* 2007, 129, 10646-10647.

(14) Ess, D. H.; Jones, G. O.; Houk, K. N. Transition States of Strain-Promoted Metal-Free Click Chemistry: 1,3-Dipolar Cycloadditions of Phenyl Azide and Cyclooctynes. *Org. Lett.* 2008, 10, 1633-1636.

(15) Ess, D. H.; Houk, K. N. Theory of 1,3-Dipolar Cycloadditions: Distortion/Interaction and Frontier Molecular Orbital Models. *J. Am. Chem. Soc* 2008, 130, 10187-10198.

(16) Bach, R. D. Ring Strain Energy in the Cyclooctyl System. The Effect of Strain Energy on [3+2] Cycloaddition Reactions with Azides. *J. Am. Chem. Soc.* 2009, 131, 5233-5243.

(17) Chenoweth, K.; Chenoweth, D.; Goddard, W. A., III Cyclooctyne-Based Reagents for Uncatalyzed Click Chemistry: A Computational Survey. *Org. Biomol. Chem.* 2009, 7, 5255-5258.

(18) Schoenebeck, F.; Ess, D. H.; Jones, G. O.; Houk, K. N. Reactivity and Regioselectivity in 1,3-Dipolar Cycloadditions of Azides to Strained Alkynes and Alkenes: A Computational Study. *J. Am. Chem. Soc.* 2009, 131, 8121-8133.

(19) Fernández, I.; Cossío, F. P.; Bickelhaupt, F. M. Aromaticity and Activation Strain Analysis of [3+2] Cycloaddition Reactions between Group 14 Heteroallenes and Triple Bonds. *J. Org. Chem.* 2011, 76, 2310-2314.

(20) Gold, B.; Shevchenko, N. E.; Bonus, N.; Dudley, G. B.; Alabugin, I. V. Selective Transition State Stabilization via Hyperconjugative and Conjugative Assistance:

(21) Gold, B.; Dudley, G. B.; Alabugin, I. V. Moderating Strain without Sacrificing Reactivity: Design of Fast and Tunable Noncatalyzed Alkyne—Azide Cycloadditions via Stereoelectronically Controlled Transition State Stabilization. *J. Am. Chem. Soc.* 2013, 135, 1558-1569.
(22) Garcia-Hartjes, J.; Dommerholt, J.; Wennekes, T.; van Delft, F. L.; Zuilhof, H. Electronic Effects versus Distortion Energies During Strain-Promoted Alkyne—Azide Cycloadditions: A Theoretical Tool to Predict Reaction Kinetics. *Eur. J. Org. Chem.* 2013, 2013, 3712-3720.
(23) Baskin, J. M.; Prescher, J. A.; Laughlin, S. T.; Agard, N. J.; Chang, P. V.; Miller, I. A.; Lo, A.; Codelli, J. A.; Bertozzi, C. R. Copper-Free Click Chemistry for Dynamic in vivo Imaging. *Proc. Natl. Acad. Sci. USA* 2007, 104, 16793-16797.
(24) Dommerholt, J.; Schmidt, S.; Temming, R.; Hendriks, L. J. A.; Rutjes, F. P. J. T.; van Hest, J. C. M.; Lefeber, D. J.; Friedl, P.; van Delft, F. L. Readily Accessible Bicyclononynes for Bioorthogonal Labeling and Three-Dimensional Imaging of Living Cells. *Angew. Chem., Int. Ed.* 2010, 49, 9422-9425.
(25) McNitt, C. D.; Popik, V. V. Photochemical Generation of oxa-Dibenzocyclooctyne (ODIBO) for Metal-Free Click Ligations. *Org. Biomol. Chem.* 2012, 10, 8200-8202.
(26) Ni, R.; Mitsuda, N.; Kashiwagi, T.; Igawa, K.; Tomooka, K. Heteroatom-Embedded Medium-Sized Cycloalkynes: Concise Synthesis, Structural Analysis, and Reactions. *Angew. Chem., Int. Ed.* 2015, 54, 1190-1194.
(27) Burke, E. G.; Gold, B.; Hoang, T. T.; Raines, R. T.; Schomaker, J. M. Fine-Tuning Strain and Electronic Activation of Strain-Promoted 1,3-Dipolar Cycloadditions with Endocyclic Sulfamates in SNO-OCTs. *J. Am. Chem. Soc.* 2017, 139, 8029-8037.
(28) Hu, Y.; Roberts, J. M.; Kilgore, H. R.; Mat Lani, A. S.; Raines, R. T.; Schomaker, J. M. Triple, Mutually Orthogonal Bioorthogonal Pairs through the Design of Electronically Activated Sulfamate-Containing Cycloalkynes. *J. Am. Chem. Soc.* 2020, 142, 18826-18835.
(29) Dommerholt, J.; Rutjes, F. P. J. T.; van Delft, F. L. Strain-Promoted 1,3-Dipolar Cycloaddition of Cycloalkynes and Organic Azides. *Top. Curr. Chem.* 2016, 374, 16.
(30) Harris, T.; Alabugin, I. V. Strain and stereoelectronics in cycloalkyne click chemistry. *Mendeleev Commun.* 2019, 29, 237-248.
(31) Deb, T.; Tu, J.; Franzini, R. M. Mechanisms and Substituent Effects of Metal-Free Bioorthogonal Reactions. *Chem. Rev.* 2021.
(32) Gold, B.; Batsomboon, P.; Dudley, G. B.; Alabugin, I. V. Alkynyl Crown Ethers as a Scaffold for Hyperconjugative Assistance in Noncatalyzed Azide—Alkyne Click Reactions: Ion Sensing through Enhanced Transition-State Stabilization. *J. Org. Chem.* 2014, 79, 6221-6232.
(33) Harris, T.; Gomes, G. d. P.; Ayad, S.; Clark, R. J.; Lobodin, V. V.; Tuscan, M.; Hanson, K.; Alabugin, I. V. Twisted Cycloalkynes and Remote Activation of "Click" Reactivity. *Chem* 2017, 3, 629-640.
(34) Ning, X.; Guo, J.; Wolfert, M. A.; Boons, G.-J. Visualizing Metabolically-Labeled Glycoconjugates of Living Cells by Copper-Free and Fast Huisgen Cycloadditions. *Angew. Chem., Int. Ed.* 2008, 47, 2253-2255.
(35) Debets, M. F.; van Berkel, S. S.; Schoffelen, S.; Rutjes, F. P. J. T.; van Hest, J. C. M.; van Delft, F. L. Aza-Dibenzocyclooctynes for Fast and Efficient Enzyme PEGylation via Copper-Free (3+2) Cycloaddition. *Chem. Commun.* 2010, 46, 97-99.
(36) Kuzmin, A.; Poloukhtine, A.; Wolfert, M. A.; Popik, V. V. Surface Functionalization Using Catalyst-Free Azide-Alkyne Cycloaddition. *Bioconjugate Chem.* 2010, 21, 2076-2085.
(37) Gordon, C. G.; Mackey, J. L.; Jewett, J. C.; Sletten, E. M.; Houk, K. N.; Bertozzi, C. R. Reactivity of Biarylazacyclooctynones in Copper-Free Click Chemistry. *J. Am. Chem. Soc.* 2012, 134, 9199-9208.
(38) Sletten, E. M.; Nakamura, H.; Jewett, J. C.; Bertozzi, C. R. Difluorobenzocyclooctyne: Synthesis, Reactivity, and Stabilization by β-Cyclodextrin. *J. Am. Chem. Soc.* 2010, 132, 11799-11805.
(39) Escorihuela, J.; Das, A.; Looijen, W. J. E.; van Delft, F. L.; Aquino, A. J. A.; Lischka, H.; Zuilhof, H. Kinetics of the Strain-Promoted Oxidation-Controlled Cycloalkyne-1,2-Quinone Cycloaddition: Experimental and Theoretical Studies. *J. Org. Chem.* 2018, 83, 244-252.
(40) Zhao, Y.; Truhlar, D. G. The M06 Suite of Density Functionals for Main Group Thermochemistry, Thermochemical Kinetics, Noncovalent Interactions, Excited States, and Transition Elements: Two New Functionals and Systematic Testing of Four M06-Class Functionals and 12 Other functionals. *Theor. Chem. Acc* 2008, 120, 215-241.
(41) Frisch, M. J.; Trucks, G. W.; Schlegel, H. B.; Scuseria, G. E.; Robb, M. A.; Cheeseman, J. R.; Scalmani, G.; Barone, V.; Petersson, G. A.; Nakatsuji, H.; Li, X.; Caricato, M.; Marenich, A. V.; Bloino, J.; Janesko, B. G.; Gomperts, R.; Mennucci, B.; Hratchian, H. P.; Ortiz, J. V.; Izmaylov, A. F.; Sonnenberg, J. L.; Williams; Ding, F.; Lipparini, F.; Egidi, F.; Goings, J.; Peng, B.; Petrone, A.; Henderson, T.; Ranasinghe, D.; Zakrzewski, V. G.; Gao, J.; Rega, N.; Zheng, G.; Liang, W.; Hada, M.; Ehara, M.; Toyota, K.; Fukuda, R.; Hasegawa, J.; Ishida, M.; Nakajima, T.; Honda, Y.; Kitao, O.; Nakai, H.; Vreven, T.; Throssell, K.; Montgomery Jr., J. A.; Peralta, J. E.; Ogliaro, F.; Bearpark, M. J.; Heyd, J. J.; Brothers, E. N.; Kudin, K. N.; Staroverov, V. N.; Keith, T. A.; Kobayashi, R.; Normand, J.; Raghavachari, K.; Rendell, A. P.; Burant, J. C.; Iyengar, S. S.; Tomasi, J.; Cossi, M.; Millam, J. M.; Klene, M.; Adamo, C.; Cammi, R.; Ochterski, J. W.; Martin, R. L.; Morokuma, K.; Farkas, O.; Foresman, J. B.; Fox, D. J. *Gaussian* 16 Rev. C.01, Wallingford, Conn., 2016.
(42) Grimme, S. Semiempirical GGA-Type Density Functional Constructed with a Long-Range Dispersion Correction. *J. Comput. Chem.* 2006, 27, 1787-1799.
(43) Glendening, E.; Badenhoop, J.; Reed, A.; E., C.; Bohmann, J.; Morales, C.; Karafiloglou, P.; Landis, C.; Weinhold, F. NBO 7.0: Natural Bond Orbital Analysis Program. *Theoretical Chemistry Institute, University of Wisconsin, Madison* (2018).
(44) In addition to 1-2-ABC-TS shown in FIG. 3, an alternative TS that resembles that for the reactions with DIBO and DIBAC was located and displays a lower $\Delta E^{\ddagger}$ (8.2 kcal/mol) but higher $\Delta G^{555}$ (22.9 kcal/mol) (Figure S1).

(45) Aronoff, M. R.; Gold, B.; Raines, R. T. 1,3-Dipolar Cycloadditions of Diazo Compounds in the Presence of Azides. *Org. Lett.* 2016, 18, 1538-1541.

(46) Aronoff, M. R.; Gold, B.; Raines, R. T. Rapid Cycloaddition of a Diazo Group with an Unstrained Dipolarophile. *Tetrahedron Lett.* 2016, 57, 2347-2350.

(47) Bickelhaupt, F. M. Understanding Reactivity with Kohn—Sham Molecular Orbital Theory: E2—$S_N2$ Mechanistic Spectrum and Other Concepts. *J. Comput. Chem.* 1999, 20, 114-128.

(48) Fernández, I.; Bickelhaupt, F. M. The activation strain model and molecular orbital theory: understanding and designing chemical reactions. *Chem. Soc. Rev.* 2014, 43, 4953-4967.

(49) Bickelhaupt, F. M.; Houk, K. N. Analyzing Reaction Rates with the Distortion/Interaction—Activation Strain Model. *Angew. Chem., Int. Ed.* 2017, 56, 10070-10086.

(50) Gold, B.; Aronoff, M. R.; Raines, R. T. Decreasing Distortion Energies without Strain: Diazo-Selective 1,3-Dipolar Cycloadditions. *J. Org. Chem.* 2016, 81, 5998-6006.

(51) Fritsch, P. IV. Ueber die Darstellung von Diphenylacetaldehyd und eine neue Synthese von Tolanderivaten. *Liebigs Ann.* 1894, 279, 319-323.

(52) Buttenberg, W. P. Condensation des Dichloracetals mit Phenol und Toluol. *Liebigs Ann.* 1894, 279, 324-337.

(53) Wiechell, H. Condensation des Dichloracetals mit Anisol and Phenetol. *Liebigs Ann.* 1894, 279, 337-344.

(54) Corey, E. J.; Fuchs, P. L. A Synthetic Method for Formyl→Ethynyl Conversion (RCHO→RC≡CH or RC≡CR'). *Tetrahedron Lett.* 1972, 3769-3772.

(55) Alexakos, P. D.; Wardrop, D. J. N-Morpholinomethyl-5-lithiotetrazole: A Reagent for the One-Pot Synthesis of 5-(1-Hydroxyalkyl)tetrazoles. *J. Org. Chem.* 2019, 84, 12430-12436.

(56) This strategy overcomes the instability of N-substituted 5-metallotetrazoles (Lesnikovich, A. I.; Levchik, S. V.; Balabanovich, A. I.; lvashkevich, O. A.; Gaponik, P. N. The Thermal Decomposition of Tetrazoles. *Thermochim. Acta* 1992, 200, 427-441).

(57) Liu, W.; Zhou, J.; Zhang, T.; Zhu, H.; Qian, H.; Zhang, H.; Huang, W.; Gust, R. Design and Synthesis of Thiourea Derivatives Containing a Benzo[5,6]cyclohepta[1,2-b]pyridine Moiety as Potential Antitumor and Anti-Inflammatory Agents. *Bioorg. Med. Chem. Lett.* 2012, 22, 2701-2704.

(58) Wardrop, D. J.; Komenda, J. P. Dehydrative Fragmentation of 5-Hydroxyalkyl-1H-tetrazoles: A Mild Route to Alkylidenecarbenes. *Org. Lett.* 2012, 14, 1548-1551.

(59) Dale, H. J. A.; Nottingham, C.; Poree, C.; Lloyd-Jones, G. C. Systematic Evaluation of 1,2-Migratory Aptitude in Alkylidene Carbenes. *J. Am. Chem. Soc* 2021, 143, 2097-2107.

(60) Littke, A. F.; Fu, G. C. Palladium-Catalyzed Coupling Reactions of Aryl Chlorides. *Angew. Chem., Int. Ed.* 2002, 41, 4176-4311.

(61) Hu, Z.; Wei, X.-J.; Hangelmann, J.; Seitz, A.-K.; Rodstein, I.; Gessner, V. H.; Goosen, L. J. Coupling of Reformatsky Reagents with Aryl Chlorides Enabled by Ylide-Functionalized Phosphine Ligands. *Angew. Chem., Int. Ed.* 2021, 60, 6778-6783.

(62) McGrath, N. A.; Raines, R. T. Diazo Compounds as Highly Tunable Reactants in 1,3-Dipolar Cycloaddition Reactions with Cycloalkynes. *Chem. Sci.* 2012, 3, 3237-3240.

(63) Mix, K. A.; Aronoff, M. R.; Raines, R. T. Diazo Compounds: Versatile Tools for Chemical Biology. *ACS Chem. Biol.* 2016, 11, 3233-3244.

(64) Caution! Unstabilized diazo compounds (e.g., diazomethane) are highly toxic and explosively reactive; their use should never be attempted in the context of chemical biology. For guidance, see: Green, S. P.; Wheelhouse, K. M.; Payne, A. D.; Hallett, J. P.; Miller, P. W.; Bull, J. A. Thermal Stability and Explosive Hazard Assessment of Diazo Compounds and Diazo Transfer Reagents. *Org. Process Res. Dev.* 2020, 24, 67-84.

(65) Andersen, K. A.; Aronoff, M. R.; McGrath, N. A.; Raines, R. T. Diazo Groups Endure Metabolism and Enable Chemoselectivity in Cellulo. *J. Am. Chem. Soc.* 2015, 137, 2412-2415.

(66) Lyles, M. M.; Gilbert, H. F. Catalysis of the Oxidative Folding of Ribonuclease A by Protein Disulfide Isomerase: Dependence of the Rate on the Composition of the Redox Buffer. *Biochemistry* 1991, 30, 613-619.

The invention claimed is:

1. A process of making a compound of formula (II):

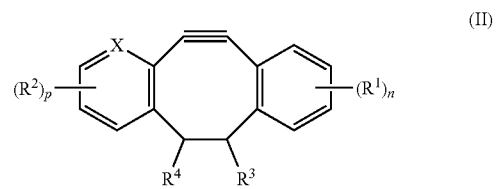

or a pharmaceutically accepted salt thereof, wherein:

$R^1$ and $R^2$ are, independently for each occurrence, F, Cl, Br, I, OTf, $B(OH)_2$, CN, $NHR^5$, $NHS(O)_2R^5$, $OR^5$, $OS(O)_2R^5$, $SR^5$, —$CF_3$, —$C(O)OC_{1-6}$ alkyl, —$C(O)N(C_{1-6}$ alkyl$)_2$, —$C(O)R^5$, $S(O)_2R^5$, $NO_2$, —$C_{1-6}$ alkyl, —$C_{1-6}$ alkenyl, or 5- to 10-membered heteroaryl substituted with 1, 2, 3, 4, or 5 $R^6$ groups, optionally wherein the alkyl and alkenyl are substituted with one or more $R^5$ group;

$R^3$ and $R^4$ are, independently for each occurrence, H or —$C_{1-6}$ alkyl;

$R^5$ is selected from H, —$C_{1-6}$-alkyl, —$CF_3$; —$C(O)OC_{1-6}$ alkyl, or —$C(O)N(C_{1-6}$ alkyl$)_2$;

$R^6$ is selected from H, F, Cl, Br, I, OTf, CN, $NH_2$, $OR^5$, $SR^5$, —$CF_3$, —$C(O)R^5$, —$C(O)OC_{1-6}$ alkyl, $NO_2$, —$C_{1-6}$ alkyl;

n is 0, 1, or 2;

p is 0, 1, or 2; and

X is CH or N;

wherein the process comprises:
(A) combining a compound of formula (III):

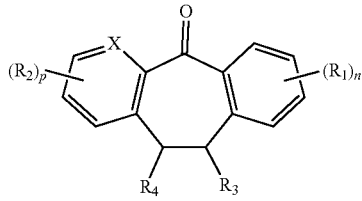   (III)

with a compound of formula (IV):

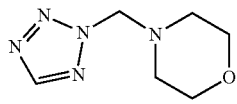   (IV)

and a non-nucleophilic base to provide the compound of formula (V):

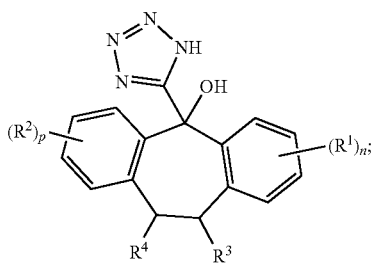   (V)

and
(B) combining the compound of formula (V) with a carbodiimide to provide the compound of formula (II).

2. The process of claim 1, wherein the compound of formula (II), has a structure according to formula (IIa):

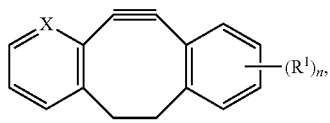   (IIa)

wherein $R^1$ is, independently for each occurrence, F, Cl, Br, I, OTf, B(OH)$_2$ or —C$_{1-6}$-alkyl;

n is 0, 1, or 2; and

X is CH or N.

3. The process of claim 1, wherein the compound of formula (II), has a structure selected from the group consisting of:

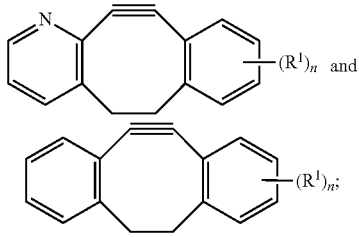

wherein $R^1$ is Cl; and n is 0 or 1.

4. The process of claim 1, wherein the compound of formula (II), has a structure selected from the group consisting of:

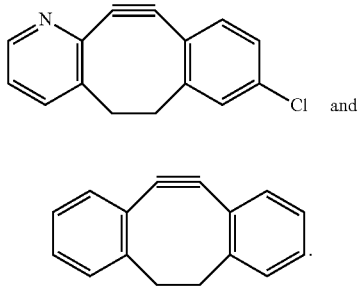

5. The process of claim 1, wherein the non-nucleophilic base is an alkyl lithium.

6. The process of claim 1, wherein the non-nucleophilic base is lithium bis(trimethylsilyl)amide.

7. The process of claim 1, wherein the carbodiimide is 1-ethyl-3-(3-dimethylaminopropyl)carbodiimide (EDC).

8. The process of claim 1, wherein step (B) comprises an alkylidene carbene rearrangement.

* * * * *